(12) United States Patent
Rohrschneider et al.

(10) Patent No.: US 8,220,455 B2
(45) Date of Patent: Jul. 17, 2012

(54) DISPENSING DEVICE

(75) Inventors: Marc Rohrschneider, Hagen (DE); Jens Besseler, Dortmund (DE); Timo Von Brunn, Berlin (DE); Ralf Thoemmes, Willich (DE); Thomas Sowden Reinhold, Muenster (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1085 days.

(21) Appl. No.: 12/121,175

(22) Filed: May 15, 2008

(65) Prior Publication Data

US 2008/0283056 A1 Nov. 20, 2008

(30) Foreign Application Priority Data

May 16, 2007 (EP) .................................. 07009803

(51) Int. Cl.
*A61M 16/00* (2006.01)
*A61M 15/00* (2006.01)
*B05D 7/14* (2006.01)
*B65D 83/06* (2006.01)

(52) U.S. Cl. .............................. 128/203.15; 128/203.21

(58) Field of Classification Search ............. 128/200.14, 128/200.22, 200.23, 203.12, 203.15, 203.19, 128/203.21; 604/58; 222/92, 95; 206/528, 206/530, 533, 538, 539, 828
See application file for complete search history.

(56) References Cited

U.S. PATENT DOCUMENTS

| | | | |
|---|---|---|---|
| 4,627,432 A | 12/1986 | Newell et al. | |
| 5,896,855 A * | 4/1999 | Hobbs et al. | 128/203.15 |
| 6,655,381 B2 * | 12/2003 | Keane et al. | 128/203.15 |
| 6,880,555 B1 | 4/2005 | Brunnberg et al. | |
| 7,451,761 B2 | 11/2008 | Hickey et al. | |
| 7,559,321 B2 * | 7/2009 | Wermeling et al. | 128/200.14 |
| 7,571,723 B2 * | 8/2009 | Braithwaite | 128/203.21 |
| 2002/0026938 A1 | 3/2002 | Hodson et al. | |
| 2003/0183229 A1 | 10/2003 | Smith et al. | |
| 2007/0151562 A1 | 7/2007 | Jones et al. | |
| 2007/0154407 A1 | 7/2007 | Peters et al. | |

FOREIGN PATENT DOCUMENTS

| | | |
|---|---|---|
| EP | 0 467 172 A1 | 1/1992 |
| EP | 1 655 050 A2 | 5/2006 |
| EP | 1 795 221 A1 | 6/2007 |
| WO | 95/11715 A1 | 5/1995 |
| WO | 01/08732 A1 | 2/2001 |
| WO | 01/17595 A1 | 3/2001 |
| WO | 01/26720 A1 | 4/2001 |
| WO | 01/72354 A2 | 10/2001 |
| WO | 01/87378 A2 | 11/2001 |
| WO | 02/13886 A2 | 2/2002 |
| WO | 2005/002654 A2 | 1/2005 |
| WO | 2006/037636 A2 | 4/2006 |
| WO | 2007/018568 A1 | 2/2007 |

* cited by examiner

*Primary Examiner* — Kristen Matter
(74) *Attorney, Agent, or Firm* — Robert Mlotkowski; Safran & Cole, P.C.; David S. Safran

(57) ABSTRACT

A dispensing device having a storage device and an air pump for dispensing a medical formulation. The storage device has multiple inserts, each insert containing a single dose of the formulation. Each insert is located in a separate and sealed cavity. The cavities can be individually opened for dispensing the respective dose from the respective insert. At least one lifespan blocking device is provided for preventing operating of the dispensing device after a predetermined number of uses corresponding to the number of receptacles.

45 Claims, 15 Drawing Sheets

DISPENSING DEVICE

BACKGROUND OF THE INVENTION

1. Field of Invention

Figure 1:
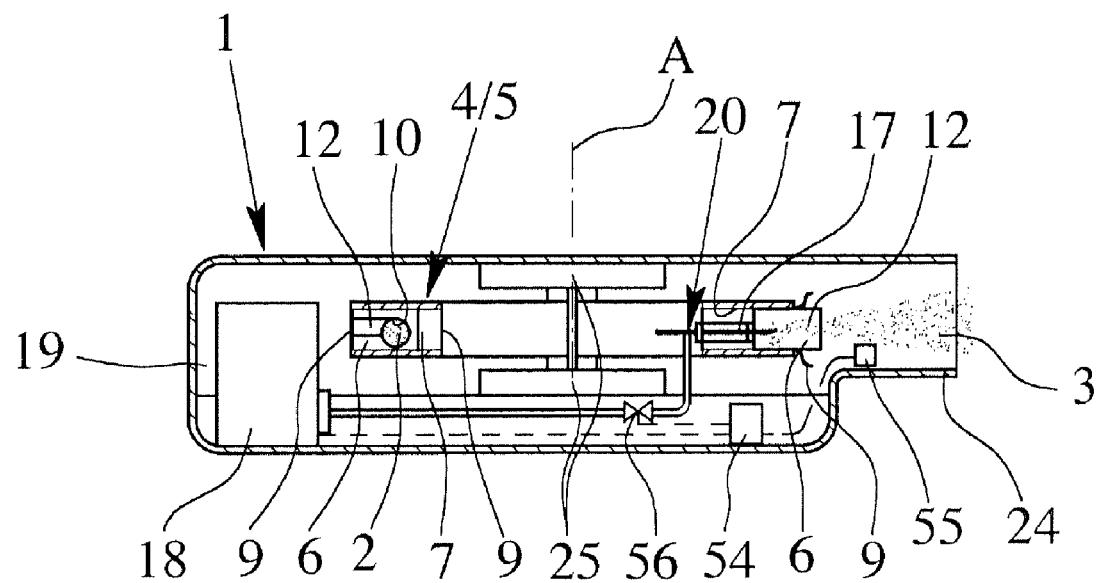

The present invention relates to a dispensing device for preferably dispensing a medical formulation, in particular one containing or consisting of a drug or mixture of drugs.

2. Description of Related Art

Drugs delivered through dispensing devices, in particular inhalers, are intended to optimally target specific sites in the pulmonary system. These sites include the nasal passages, the throat, and various locations within the lungs, such as the bronchi, bronchioles and alveolar regions. The ability to deliver drugs to a target area depends inter alia on the aerodynamic sizes of the particles or droplets. As currently believed to be understood, particles having an aerodynamic diameter of less than 2 micrometer are considered to be potentially optimal for deposition in the alveolar region of the lung. Particles that have an aerodynamic diameter of between 2 and approximately 5 micrometer may be more suitable for delivery to the bronchiole or bronchi regions. Particles with an aerodynamic size range greater than 6 micrometer, and more preferably 10 micrometer, are typically suitable for delivery to the laryngeal region, throat or nasal passages.

In most cases, it is desired to achieve a high inhalable fraction and a high delivery efficiency, i.e., the fraction of the initial dose of drug that reaches the desired region, in particular, in the lung. This depends on various factors, in particular, on the characteristics of the generated spray plume, such as propagation velocity of the plume, particle size and its distribution, fraction of small particles, fraction of gas or the like.

U.S. Pat. No. 4,627,432 discloses a device for administering medicaments to patients, namely an inhaler. The inhaler comprises a disk-like blister pack having a plurality of blister pockets arranged in a circle. Each blister pocket contains a dose of the powder. A plunger can open a blister pocket. When a blister is opened, the medicament can be withdrawn by a patient inhaling through a mouthpiece.

International Patent Application Publication WO 2005/002654 A2 discloses a passive device for dispensing individual doses of powder. The doses are contained in respective pockets of a disc-shaped carrier and opened by outwardly rupturing a lidding foil in axial direction by means of pressure on an opposite side surface. The pockets are moveable in an axial direction into an airstream generated by breathing of a patient for dispensing a dose of powder from the pocket. The device provides individual respective deaggregation flow paths for each pocket, split airstreams allowing improved entrainment of powder, a cam mechanism for outwardly rupturing the pockets, an indexing mechanism linked to the cam mechanism, and a dose counter.

It is difficult to empty the respective pocket completely during a dispensing operation. Incomplete emptying results in decreased delivery efficiency. Some powder may be lost in the inhaler and not dispensed because the known solutions require relatively long paths for the powder until the powder reaches a nozzle and is actually dispensed. This might reduce the delivery efficiency further. In addition, de-agglomeration of the powder is difficult.

International Patent Application Publication WO 2006/037636 A2 discloses an active dispensing device with an air pump for dispensing powder separately from storage chambers in a common carrier. Preferably, an individual deaggregation and outlet duct having a flat cross-section is associated to each storage chamber.

SUMMARY OF THE INVENTION

In accordance with the present invention, the desired spray plume characteristics include, preferably, a small particle size, a high fraction of drug particles with a diameter of 6 micrometer or less, a low propagation velocity and/or a long duration of spray generation and possible inhalation.

The present invention relates to the dispensing of a preferably medical formulation. The term "formulation" relates, in particular, to powder, but may include or relate to liquid as well. Consequently, the fine "particles" may be either solid or liquid. The term "liquid" has to be understood preferably in a broad sense covering inter alia solutions, suspensions, suslutions, mixtures thereof or the like. More particularly, the present invention relates to the dispensing of formulations for inhalation, such as medical formulations containing or consisting of at least one drug.

In the following, the description will focus mainly on powder formulations. However, the same applies for liquid formulations.

In particular, the present invention is concerned with dry powder inhalers for the delivery of drugs to the lungs. Many dry powder inhalers are on the market or have been proposed. There are two main types, namely, the passive ones and the active ones. In passive inhalers, all the energy required for de-agglomerating the powder and transferring the powder to the lungs is provided by the breathing of a user, respectively the patient. In active inhalers, there is an additional source of energy to help to transfer and de-agglomerate the powder.

Most powder inhalers are of the passive type where the powder is inhaled by the patient without the aid of an additional energy source. The problem with passive inhalers is that the inhalable fraction, or the proportion of powder that actually enters the lungs, is largely dependent on the breathing of the patient. The transfer and de-agglomeration of the powder, and hence the inhalable fraction, is a function of the flow rate of inhaled air through the device, and therefore, varies greatly from patient to patient.

Dry powder inhalers are subdivided into single dose and multi-dose devices or inhalers. Multi-dose inhalers are further subdivided into pre-metered types where the doses are stored individually and into metering inhalers where each powder dose is metered in the device.

Multi-dose pre-metered inhalers have the advantage that the single doses are metered under strict factory conditions and the powder can quite easily be isolated from the atmosphere. In many applications, the active drug powder is mixed with a carrier, such as lactose. The lactose and/or active drug(s) tend to absorb humidity from the atmosphere, which makes them stick together and difficult to transfer and de-agglomerate.

The present invention relates, in particular, to an active, gas (preferably air) powered, pre-metered multi-dose dispensing device for dispensing a formulation containing or consisting of a drug, such as a dry powder inhaler.

A primary object of the present invention is to provide an improved dispensing device, in particular wherein a compact construction, easy handling or operation, a high delivery efficiency and/or desired spray plume characteristics can be achieved.

The above object is achieved by a dispensing device wherein the dispensing device is adapted to receive, or comprises, a storage device with multiple separate and pre-metered doses of the formulation in receptacles that are, preferably, annularly arranged, wherein the dispensing device comprises a transport mechanism for moving, in particular, rotating, the storage device to the next receptacle, and wherein the dispensing device comprises one or more lifespan blocking means.

According to present invention, the dispensing device comprises multiple, in particular, three, lifespan blocking means. In particular, the blocking means are at least partly formed by the storage device, preferably by a common carrier supporting multiple receptacles of the storage device. This allows a compact and simple construction and/or easy and secure handling and operation.

According to one preferred aspect of the present invention, an actuator, in particular a grip, of the dispensing device is radially movable or operable to rotate the storage device to the next receptacle and/or to radially move the connecting element in order to individually open the respective receptacle and/or to connect a gas supply or pump to the respective receptacle and/or to push an insert out of the respective receptacle. This allows a compact construction and/or easy handling or operation.

Another preferred aspect of the present invention is that the dispensing device comprises a means for preventing a backstroke of the connecting element during dispensing. This allows easy handling or operation and ensures high delivery efficiency and/or desired spray plume characteristics.

According to a further preferred aspect of the present invention, the dispensing and storage device comprise means for aligning the connecting element and the respective receptacle, wherein said means comprise guiding portions formed at or by the storage device and/or the receptacles. This ensures correct alignment and, thus, the desired dispensing with high delivery efficiency and/or desired spray plume characteristics, wherein compact construction and easy handling or operation are possible.

According to another preferred aspect of the present invention, the dispensing device or storage device comprises means for limiting the movement of the inserts. This allows a compact and simple construction and easy handling or operation.

According to a further preferred aspect of the present invention, the dispensing device comprises means for reinserting the inserts into the respective receptacles after use. This allows a compact and simple construction and/or easy handling or operation.

According to another further aspect of the present invention, the storage device comprises a common carrier, wherein the receptacles are separate parts mounted on the carrier by clipping, snapping, pressing and/or clamping. This allows a compact and simple construction and, in particular, an optimized filling of the receptacles, preferably of inserts of the receptacles, with the dosed formulation.

According to another preferred aspect of the present invention, the storage device comprises an empty or hollow or dummy receptacle into which the connecting element can engage in a state before first use or when mounting the dispensing device. This allows a compact and simple construction and, in particular, facilitates mounting of the dispensing device.

According to another preferred aspect of the present invention, the storage device comprises inserts that are moveable within respective cavities or receptacles for dispensing, wherein each insert comprises a tip portion or other opening means and/or is tapered in order to facilitate opening of an associated seal by movement of the respective insert against or through the sealing. This allows a compact and simple construction and/or easy and secure handling and operation.

According to a further preferred aspect of the present invention, the dispensing device comprises detection means for detecting inhalation or breathing in and/or trigger means for triggering dispensing of the respective dose by means of pressurized gas. This allows easy and simple handling and operation.

Preferably, each insert comprises at least one channel and/or nozzle arrangement in order to directly form the spray during use. Thus, the spray is generated by the respective insert when pressurized gas is supplied. This makes it possible to respectively generate sprays with the desired spray plume characteristics with high accuracy.

Further aspects, advantages and features of the present invention will be apparent from the following detailed description of preferred embodiments in conjunction with the accompanying drawings.

BRIEF DESCRIPTION OF THE DRAWINGS

FIG. 1 is a schematic sectional view of a dispensing device with a storage device according to one embodiment of the present invention during dispensing;

FIG. 2 is a schematic section of the storage device with an insert;

FIG. 3 is a schematic sectional view of the insert;

FIG. 4 is a schematic sectional view of the insert taken along line IV-IV of FIG. 3;

FIG. 5 is a schematic sectional view of another insert;

FIG. 6 is a schematic sectional view similar to FIG. 4 of the insert, but taken along line VI-VI of FIG. 5 and with a carrier and an inserted piercing element;

FIG. 7 is a schematic perspective view of a dispensing device according to a further embodiment of the present invention;

FIG. 8 is a schematic view of inner components of the dispensing device according to FIG. 7 with retracted air assembly;

FIG. 9 is a schematic view of inner components of the dispensing device according to FIG. 7 with advanced air assembly in an activated state;

FIG. 10 is a schematic view of inner components of the dispensing device according to FIG. 7 with advanced air assembly after dispensing;

FIG. 11 is a schematic view of a receptacle of a storage device;

FIG. 12 is a schematic view of a carrier of the storage device;

FIG. 13 is a partial enlarged view of the carrier according to FIG. 12;

FIG. 14 is another partial enlarged view of the carrier according to FIG. 12;

FIG. 15 is a schematic perspective view of a needle holder of the air assembly;

FIG. 16 is a schematic, partially sectional perspective view of the dispensing device according to FIG. 7 with a pulled grip; and FIG. 17 is a schematic view of a half of the housing of the dispensing device according to FIG. 7.

DETAILED DESCRIPTION OF THE INVENTION

In the figures, the same reference signs are used for the same or similar parts and components, wherein the same or similar features, aspects and/or advantages are achieved in the different embodiments, even if a repetition of the respective description is omitted.

FIG. 1 shows in a schematic sectional view—for illustration purposes not in scale—a dispensing device 1 according to the present invention. The dispensing device 1 is preferably an active device, in particular, gas powered. Preferably, the dispensing device 1 is an oral or nasal inhaler, in particular a dry powder inhaler, for a user, respectively the patient (not shown).

Preferably, the dispensing device 1 is portable and/or handheld.

The dispensing device 1 may be used for dispensing any formulation 2 as defined in the introductory part of the description. In particular, a medical formulation 2 or a formulation 2 for inhalation will be used. The formulation 2 preferably contains or consists of at least one drug. When the formulation 2 is dispensed, a spray 3 is generated as indicated in FIG. 1. The spray 3 includes or consists of fine particles (solid and/or liquid) and preferably has the desired spray plume characteristics.

The formulation 2 may be a liquid, in particular a solution, a suspension or any mixture thereof, i.e. a so-called suslution. Preferably, when different drugs are dispensed simultaneously, a suslution may be used. The principle of the suslution is based on that different drugs may be combined in one formulation simultaneously as a solution and as a suspension. In this respect, reference is made to EP 1 087 750 A1, which is incorporated herein as additional disclosure in this respect.

Preferably, the formulation 2 is a powder. The powder may be a pure drug or a mixture of at least two drugs or any other mixture of at least one drug. In addition, the powder may contain at least one other material, in particular a drug carrier such as lactose. In the following, the description focuses on powder as formulation 2. However, this applies in a similar manner if a liquid formulation 2 is used.

Preferably the mean diameter of the powder particles is about 2 to 7 micrometer, in particular 6 micrometer or less. This applies in particular if the powder does not contain any drug carrier such as lactose.

If the powder contains a drug carrier, such as lactose, and at least one drug, the powder 2 may have a particle size of 20 to 300 micrometer, in particular about 30 to 60 micrometer. However, the de-agglomeration, which will be described later in more detail, may result even in this case in a spray 3 with a smaller particle size, e.g. of about 10 micrometer or less. In particular, the drug may be separated from the drug carrier during de-agglomeration so that primarily the drug will be inhaled due to its small particle size of about 2 to 6 micrometer and the larger drug carrier will be swallowed when using the dispensing device as an inhaler. Alternatively or additionally, breaking or opening of the drug carrier is possible during de-agglomeration.

The diameters mentioned above and below may be understood as mass medium aerodynamic diameters and/or may apply to the particle size or a fraction of the particles of the spray 3.

Preferably, the formulation 2 is premetered in separate or individual doses, which can be discharged one after the other by the dispensing device 1, in particular for inhalation.

The dispensing device 1 is adapted to receive or comprises a storage device 4 for storing preferably multiple and pre-metered doses of the formulation 2. The storage device 4 may be integrated into the dispensing device 1 or form part of the dispensing device 1. Alternatively, the storage device 4 may be a separate part that can be inserted or connected with the dispensing device 1 and optionally replaced.

Figure 2:
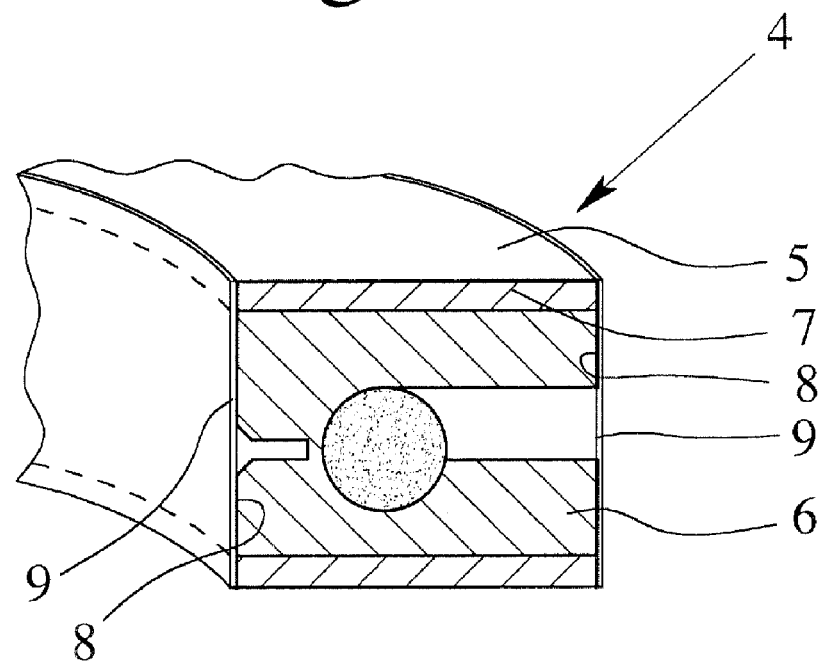

FIG. 2 shows a schematic cross-section of the preferably ring-like storage device 4.

The storage device 4 preferably comprises a carrier 5 and at least one insert 6, preferably multiple inserts 6. In particular, the carrier 5 may comprise or support 20 to 100 inserts, but preferably 30 to 60 inserts 6. Each insert 6 preferably contains one pre-metered dose of the formulation 2. However, each insert 6 may also contain more than one formulation 2, i.e., different formulations 2. Additionally or alternatively, different inserts 6 may contain different formulations. In the context of the present invention, "different" means, in particular, that the formulations 2 differ in at least one of the composition, the drug, the dose or amount, the concentration, and consistency of the formulation 2, e.g., liquid or dry powder.

The storage device 4 or carrier 5 preferably comprises multiple cavities 7 or receptacles for receiving or containing the inserts 6. In particular, each insert 6 is located in a separate cavity 7. Preferably, the cavities 7 are separate from each other, and in particular, are sealed relative to each other.

In the present embodiment, each cavity 7 comprises at least one opening 8, in particular two, preferably opposed openings 8 (here, at the radially inner and outer circumference or periphery).

The cavities 7 or its openings 8 are covered by respective covers or seals 9 which are preferably formed by heat-sealed foils on opposite sides of the respective cavity 7 or the carrier 5. In the present embodiment, the seal 9 is, in particular, a metallic foil, such as aluminum foil, plastic foil, a multi-layer arrangement or the like. The seals 9 preferably protect the inserts 6 and/or formulation 2 against humidity, dirt, moisture and/or the like. The seals 9 are respectively resistant and/or impermeable, in particular, gas-tight.

In this preferred embodiment, the storage device 4 or carrier 5 is ring-shaped and the cavities 7 extend at least substantially in a radial direction. The cavities 7 are distributed around the perimeter of or along the storage device 4 or carrier 5, preferably equally spaced relative to the adjacent cavities 7.

In the present embodiment, the storage device 4/carrier 5 is preferably rotatable around axis "A" shown in FIG. 1. In particular, the dispensing device 1 can be opened and the storage device 4/carrier 5 can be inserted or replaced.

The carrier 5 may be a molded element, a ring, a strip, a cartridge, a blister or a container. Preferably, the storage device 4 or carrier 5 is rigid or at least essentially stiff.

Preferably, the carrier 5 is made of foil, plastic, ceramic and/or a composite material, in particular, a thermoplastic or thermoplastic elastomer.

Each cavity 7 or receptacle preferably forms a guide for the associated insert 6, in particular, so that the insert 6 is moveable in at least one direction and/or at least partially out of the cavity 7 or receptacle.

FIG. 1 shows a situation, where the insert 6 on the right side has already been pushed partially out of its associated cavity 7 and/or the outer opening 8 and/or through the respective seal 9 of its associated cavity 7 for opening the seal 9. The insert 6 shown on the left side of FIG. 1 is still within its closed and sealed cavity 7.

Each insert 6 is preferably produced filled with the respective dose of formulation 2 separately from the storage device 4 or carrier 5 and, then, inserted into its respective cavity 7 or receptacle.

Preferably, each insert 6 is molded and/or made of foil, plastic, ceramic and/or composite material, in particular, of thermoplastic or a thermoplastic elastomer, and for seals, of elastomers or silicone.

According to a preferred embodiment, the carrier 5 and/or the inserts 6 are made of at least one of the following materials or any mixture or blend thereof: ABS (acrylonitril-butadiene-styrene copolymer); SAN (styrene-acrylonitril-copolymer); PBT (polybutylene terephthalate); PC (polycarbonate); CA (cellulosic acetate); EVA (ethylene vinylacetate copolymer); PA (polyamide); PE (polyethylene); PP (polypropylene); PMMA (polymethylmethacrylate); POM (polyoxymethylene, polyacetal); PPS (polyphenylene sulfide); PS (polystyrene); PBTP (polybutylene terephthalate); TPU (thermoplastic polyurethane); blend of PC and PBTP; blend of PC and ABS; LCP (liquid crystal polymers); PHCS (polypyrrol or polythiophene); PPA (polyphthalamide); PSU (polysulfone); PTFE (polytetrafluorethylene); PUR (polyurethane); SB (styrene-butadiene copolymer); PIB (polyisobutylene); PAN (peroxyacylnitrate); PET (polyethylene terephthalate); AMMA (acrylonitril-methymethacrylat copolymer); PAR (polyarylate); PEEK (polyetheretherketone); COC (cycloolefine copolymer).

Each insert 6 may form a preferably block-like unit and/or be rigid. Alternatively, the inserts 6 may be flexible. In particular, each insert 6 may be a unitary unit or formed of multiple elements. In particular, the insert 6 forms a unitary component or is made of one piece. Each insert 6 may be a molded element, a cartridge, a blister, a capsule, a container or the like.

In the following, a preferred construction of one insert 6 is explained. Preferably, all inserts 6 are identical. However, it is also possible that the all or some of the inserts 6 are different. For example, two or more groups of different inserts 6 can be provided. It is possible that one group has a different dosage or a different formulation 2 than the other group. For example, the inserts 6 of the different groups could be arranged alternately one after the other so that a patient or user may use, for example, each morning an insert 6 of one group and each evening an insert 6 of the other group.

Figure 3:
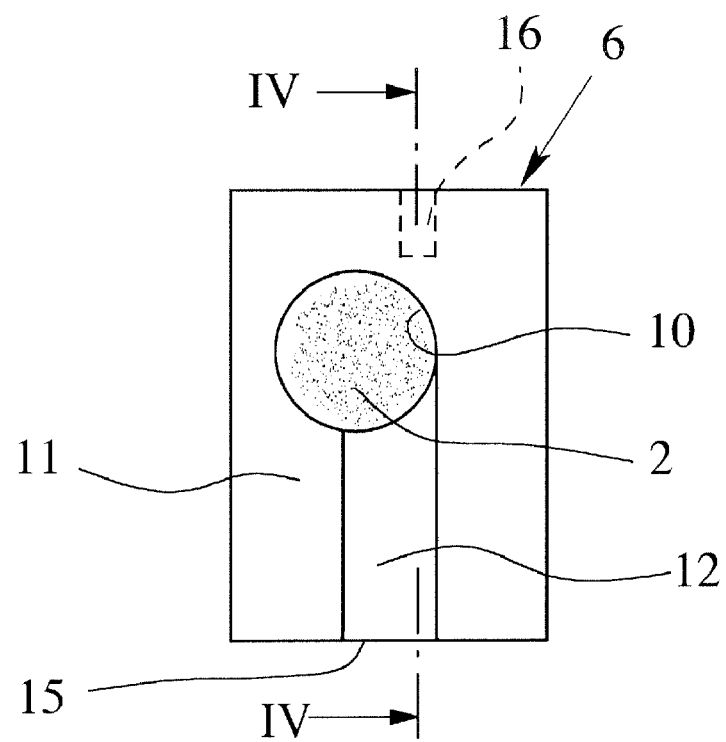
Figure 4:
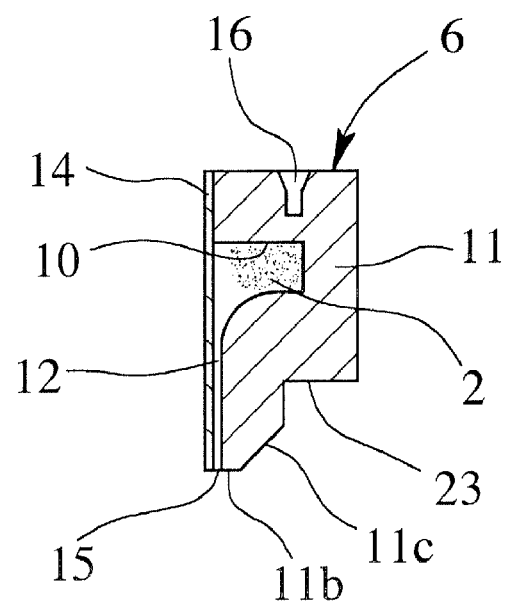

Each insert 6 preferably comprises a storage chamber 10 for a single dose of the formulation 2. The schematic sectional view according to FIGS. 2 & 3 and the schematic sectional view according to FIG. 4, which is a view along line IV-IV of FIG. 3, show one preferred embodiment of the insert 6. The insert 6 comprises a storage chamber 10 for the formulation 2. In the present embodiment, the storage chamber 10 is preferably formed in a molded base member 11 of the insert 6.

The insert 6/base member 11 further comprises a duct 12 or the like for deagglomerating and/or discharging the formulation 2 during the dispensing operation. The formulation 2 is dispensed through the duct 12 during the dispensing operation, in particular for de-agglomerating the powder and/or forming the spray 3.

Preferably, the duct 12 is flat and/or rectangular in cross section. In particular, the cross section corresponds to a hydraulic diameter of less than 1 mm. In particular, the duct 12 is designed as described in International Patent Application Publication WO 2006/037636 A2, which is incorporated herein by reference.

According to another (unillustrated) embodiment, the duct 12 can also be used as a reservoir (storage chamber 10) for the formulation 2. In this case, the separate storage chamber 10 is not required. Then, the duct 12 is designed to enable sufficient mixing of the gas with the formulation 2 and sufficient de-agglomeration of the powder formulation 2.

Preferably, the spray 3 having its desired spray characteristics is directly ejected or discharged from the insert 6/duct 12.

As noted above, the insert 6 is formed as unitary component or is made of one piece. The insert 6 or duct 12 can comprise a nozzle arrangement 13, preferably, at an outlet 15 or end of duct 12 or formed by duct 12, as shown in the schematic longitudinal sectional view of another embodiment according to FIG. 5.

Preferably, the storage chamber 10 and/or the duct 12/nozzle 13 is formed by or in the base member 11, in particular, by a recess, groove or the like in the base member 11 and by an associated cover member 14 as shown in FIG. 4. In particular, the duct 12 forms a channel from the storage chamber 10 to the outlet 15 of the insert 6, in particular, for directly discharging or dispensing the formulation 2 as spray 3 as shown in FIG. 1. Preferably, the base member 11 is molded and/or rigid. Preferably, the cover member 14 is rigid and/or is welded to the base member 11.

It is noted that the inserts 6 may be or are preferably open, i.e., not sealed, in particular, at their respective outlet 15 only since experiments have shown that sealing of the carrier 5/the cavity 7 is sufficient. The duct 12/nozzle arrangement 13 is preferably so small in cross section or is provided with a bursting element or any other suitable means that insures that the formulation 2 is not discharged, even with an opened seal 9 and/or during strong shaking of the dispensing device 1/storage device 4, but rather is discharged only when gas (air) is forced through the insert 6 and duct 12.

The storage device 4 may comprise only one insert 6 with one storage chamber 10 for a single dose or can be provided with multiple storage chambers 10 with different formulations 2. In the preferred embodiment, each insert 6 is for a single dose and/or single use only, but the storage device 4 preferably comprises multiple inserts 6 and, thus, contains multiple doses of the formulation 2, which can be dispensed subsequently.

Further, the inserts 6 and cavities 7 are preferably adapted to each other such that the seals 9 contact end faces of the inserts 6, and thus, cover the outlets 15. This may further prevent any formulation 2 from dissipating through the duct 12/outlet 15 before the desired dispensing. In order to increase the seal or cover effect of seal 9, the inserts 6 may be slightly longer than the cavities 7 and/or protrude at their outlet side and/or be pressed with their outlets 15 against the seals 9 or vice versa.

Preferably, the nozzle arrangement 13 forms a means for slowing down the velocity as shown in the embodiment of FIG. 5. This means forms, here, a multiple jet impinging means. The means forms multiple—at least two—jets P which impinge, i.e., hit, each other, as indicated in FIG. 5. In this embodiment, the duct 12 divides into two sections 12*a*, 12*b* that are designed such that the openings or outlets 15 are angled toward each other so that the jets P ejected from the sections 12*a*, 12*b* impinge. For example, a flow divider 11*a* or any other guiding means can be located in the flow path to form the at least two sections and/or last sections 12*a*, 12*b* of the duct 12 as shown in FIG. 5.

The embodiment according to FIG. 5 is also suitable for impinging more than two jets P. For example, it is possible to have similar arrangements in the cross sectional planes perpendicular to the drawing plane resulting in four outlet directions and jets P arranged on the surface of a conus. However, multiple other arrangements with similar effects are possible.

The impinging angle W between the jets P is between 30 and 180 degrees, preferably at least 90 degrees for powder, in particular, about 90 to 150 degrees.

The impinging of the jets P results in a decrease of the velocity of the spray 3 and/or in a de-agglomeration of the powder or forming of small droplets and/or in separation of drug particles from a carrier and/or in better focusing of the spray 3. These effects depend on the impinging angle W. A larger impinging angle W tends to result in better effects. In contrast to liquid jets, an impinging angle W of 90 degrees or more is possible and preferred for powder.

Alternatively, the nozzle 13 or any other suitable nozzle arrangement could be used instead of or in any other combination with duct 12.

FIG. 6 shows a schematic sectional view of the insert 6 taken along line VI-VI of FIG. 5, wherein the insert 6 is housed in its cavity 7/storage device 4, but has already moved somewhat outward of one opening 8.

The insert 6 preferably has an inlet for supplying preferably pressurized gas into the storage chamber 10 to force the formulation 2 through the duct 12/nozzle arrangement 13 and directly generate the described spray 3. In the present embodiment, the inlet is preferably formed by a weak or thinned portion and/or is designed as a preferably tube-like recess 16 or blind bore formed in the base member 11. Preferably, the recess 16 is not directly connected to the storage chamber 10, but is separated by a seal or an intermediate or thinned wall or the like. This wall can be penetrated, e.g., by a piercing element 17, such as a needle as shown schematically in FIG. 6 or by any other suitable opening, connecting and/or supply means, in particular, when the respective insert 6 is connected to a gas supply as explained in the following. Preferably, the piercing element 17 is a hollow needle with a solid or closed tip 17a and a side opening 17b adjacent the tip 17a for supplying the pressurized air into the insert 6/storage chamber 10.

In the present invention, the expression "piercing element 17" preferably covers also all other suitable types of means for opening and/or connecting the storage device 4, the carrier 5, a cavity 7 and/or an insert 6 and/or for directly or indirectly supplying gas to an insert 6 or its respective storage chamber 10.

It is noted that the cross sections of the inserts 6 and the cavities 7 are preferably polygonal, in particular, rectangular or that other guiding means are preferably provided, in order to avoid that the inserts 6 rotate within the cavities 7. However, if the inserts 6 are rotatably symmetrical with respect to the recess 16 or any other connection/inlet for gas supply and with respect to its outlet 15, the inserts 6 may also be cylindrical and/or can rotate within the cavities 7. This may facilitate insertion of the inserts 6 into the cavities 7 during production.

Figure 5:
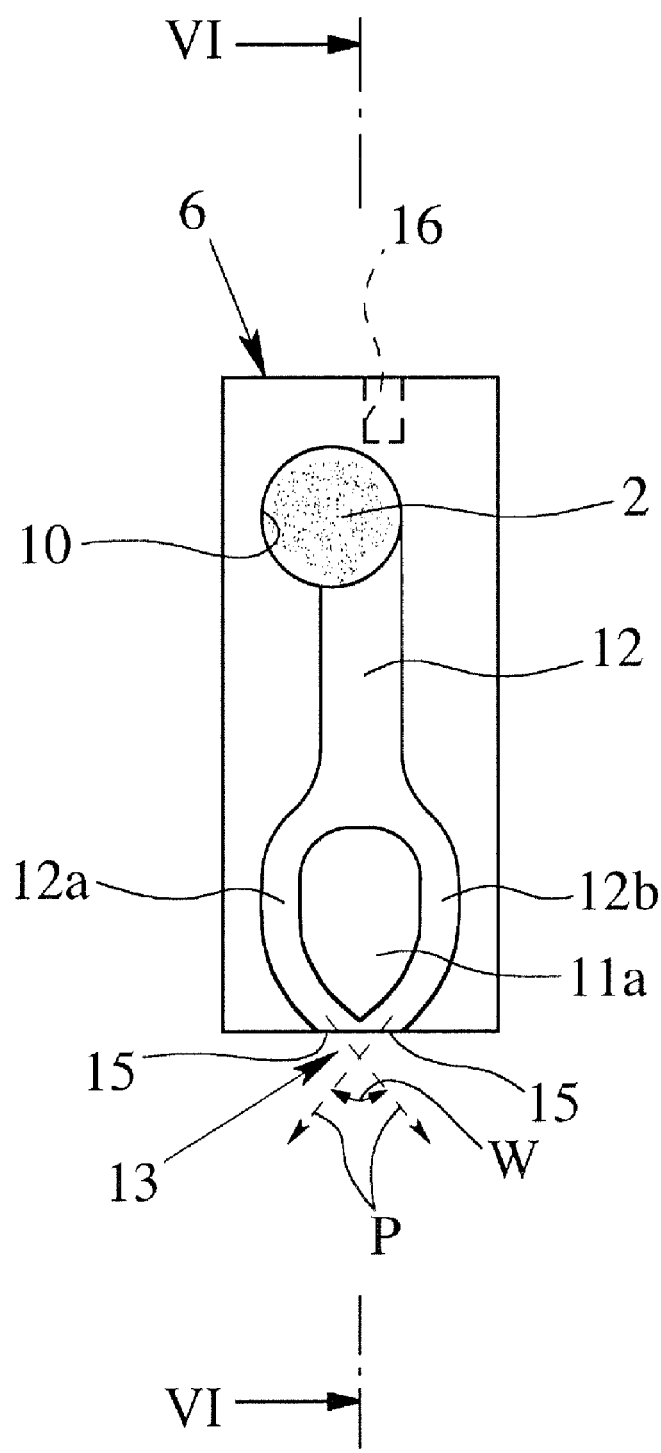
Figure 6:
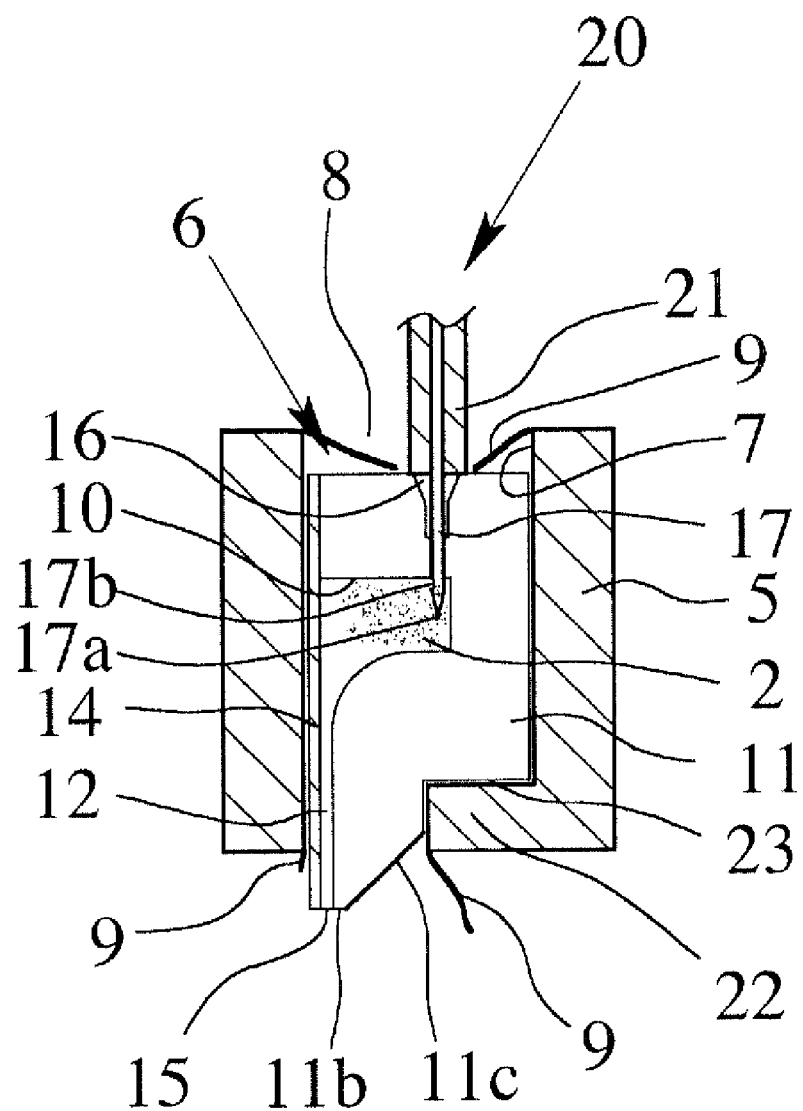

The duct 12 is preferably at least tangentially connected to the storage chamber 10 as shown in FIGS. 3 & 5. Preferably, the duct 12 is connected at one axial end of the preferably cylindrical chamber 10, and the gas inlet (recess 16/piercing element 17) is connected or connectable to the other axial end of the chamber 10 as indicated in FIG. 6. In particular, the gas inlet is connected also tangentially to the storage chamber 10, such that swirls are generated by the entering gas with a swirl direction supporting discharge of the mixture of gas and formulation 2 through the duct 12, which connects tangentially to the rotational direction of the swirl.

The dispensing device 1 uses preferably pressurized gas, in particular air, to force the formulation 2 through the duct 12/nozzle arrangement 13 to de-agglomerate the powder and/or to generate the spray 3 with fine powder particles. Preferably, the dispensing device 1 comprises a means for providing pressurized gas, in the present embodiment, an air pump 18, as indicated in FIG. 1, which can preferably be actuated or operated manually, e.g., as indicated, by a handle or actuator 19 and/or by a spring means as shown later in another embodiment. In particular, the air pump 18 comprises or is formed by a bellows. But, it could also be a piston-cylinder-arrangement. Instead of the air pump 18, the means for providing pressurized gas can be, e.g., a capsule, container or the like containing pressurized or liquefied gas for powering the dispensing device 1, i.e., dispensing the formulation 2 as desired. Therefore, the term "means for pressurizing gas" is to understood in a broad sense to cover these and similar alternatives to the pump 18 as well.

The means for providing pressurized gas/air pump 18 may provide a gas pressure of less than 300 kPa, in particular, about 50 to 200 kPa. This is preferably sufficient for operating the dispensing device 1. If liquefied gas or a container with pressurized gas is used, the gas pressures might range from 100 kPa to about 700 kPa. Then, the pressure may be reduced or throttled to the preferred pressure range before supplying the gas to the storage device 4, in particular, the storage chamber 10 of the respective insert 6.

Preferably, all pressure values mentioned in the present description are gauge pressures, i.e., pressure differences. All pressure values relate to the pressure in a gas storage, such as a container with pressurized or liquefied gas or provided by air pump 18 or relate to the pressures acting in the chamber 10 and/or in the duct 12.

FIG. 1 shows that the dispensing device 1 preferably comprises a mechanism 20 for individually opening the cavities 7, for individually moving the inserts 6, preferably radially (here outwardly) and/or through an associated opening 8 and/or seal 9, and/or for individually connecting the inserts 6 to the gas supply, in particular to the air pump 18. The mechanism 20 comprises preferably the piercing element 17 and/or any other suitable connecting or actuation element.

In particular, in a first operation phase the piercing element 17 penetrates the seal 9, and then, is inserted into the recess 16 and through the intermediate end or weakened wall into the storage chamber 10, and thus, connects the respective insert 6 to the gas supply. Before, simultaneously or afterwards, e.g., during the further movement, the mechanism 20 pushes the insert 6 through the other or outer opening 8 and through the respective seal 9 at least partially out of its cavity 7. Preferably, the mechanism 20 acts directly on the respective insert 6 to cause its movement. Here, the piercing element 17 is preferably provided with a shoulder or abutment or sleeve 21 (shown schematically in FIG. 6) abutting at the insert 6 to positively cause the desired movement of the insert 6 when moving the mechanism 20/piercing element 17. The final situation is shown in FIG. 1 on the right side and in FIG. 6 with protruding insert 6.

It is noted that any other driving mechanism can be used to move the insert 6 to open one opening 8/one seal 9/respective outlet 15 or the insert 6 itself. In particular, it is possible to realize the preferred pushing of the insert 6 through the seal 9 independently of the connecting or piercing of the insert 6.

In order to facilitate opening of the respective seal 9, the insert 6 preferably comprises an opening means, in particular, a tip portion 11*b*, and/or is tapered at its outlet end. In particular, the insert 6 or its base 11 comprises an inclined portion 11*c*—preferably at least or only on one flat side of the insert 6 or base 11—so that the insert 6/base 11 is tapered towards the outlet 15, as shown schematically in FIGS. 4 & 6. Thus, it is possible to form a tip or tip portion 11*b*, which forms a front face with a reduced or minimal surface. It is even possible to form a cutting edge at the outlet end.

Alternatively or additionally, it is possible to form or provide any other suitable cutting element as an opening means at the insert 6, in particular, at its outlet end.

In particular, the stroke or outward movement of the insert 6 is adapted and preferably is so long that the desired opening of the seal 6 is ensured, and in particular, that the broken, cut and/or rupture parts of the opened seal 9 cannot hinder or cover or interfere with the outlet 15 of the insert 6. In the present embodiment, the seal 9 substantially ruptures at one side of the opening 8 where the tip portion 11*b* of the insert 6 is located. The short rest than the seal 9 mounted on this side of the opening 8 cannot interfere with the outlet 15 of the protruding insert 6 is if it is shorter than the outward stroke of the insert 6 so that the longer part of the seal 9 connected to the other side of the opening 8 will be bent or pivoted away by the insert 6.

In the present embodiment, the opening and/or cutting of the seal 9 takes place at one side or adjacent to one edge of the preferably rectangular opening 8 when the respective insert 6 is moved outward of its cavity 7 for activating and later dispensing. The opening means, tip portion 11b, cutting element or the like is located at one side of the insert 6, and in particular, adjacent to one side of its cavity 7 and opening 8 so that the mentioned opening of the respective seal 9 occurs as described when the insert 6 is moved outward. In other words, the location of the opening or cutting means may be and, in particular, is used to ensure or cause a desired opening pattern and/or location of the respective sealing, in particular, at one side and/or adjacent to one edge of the opening 8. However, other opening locations can be chosen. For example, it is also possible to open the respective seal 9 in the center. Additionally or alternatively, the insert 6 may be adapted—in particular, by provision of two or more opening or cutting means—to open or rupture or cut the respective seal 9 at multiple regions subsequently or simultaneously.

In the present embodiment, the insert 6 is preferably moveable radially and/or outwardly and/or away from the airpump 18 and/or in its longitudinal direction and/or in the main discharge direction and/or in the main extension of the mouthpiece 24. However, other movements are also possible. In the present case, only a translational movement is produced. However, a rotational or pivotal movement can be produced additionally or alternatively or superposed.

Preferably, the storage device 4, the carrier 5 and/or the cavities 7 comprise means for limiting the possible or maximum movement of the inserts 6. Preferably, this means stops the insert(s) 6 by form-fit. In the present embodiment, the means comprise stops 22, e.g., shoulders, protrusions or the like, which interact with a respective abutment, such as a shoulder 23, of the respective insert 6 so that the insert 6 is limited in its movement out of the respective cavity 7 as shown schematically in FIG. 6 where the shoulder 23 abuts the respective stop 22 and, thus, prohibits any further outward movement of the insert 6. However, it is noted that any other technical solution having the same effect can also be used.

For dispensing, the gas is supplied under pressure to the storage chamber 10 via the piercing element 17 or any other suitable supply element.

The gas (air) generates a respective flow in the storage chamber 10 to mix gas and powder and to force the dose through the duct 12.

The powder will be discharged—in particular forced through the duct 12—with a comparatively low gas pressure (preferably less than 300 kPa, in particular about 50 to 200 kPa). This low gas pressure, which is significantly lower than the gas pressures in the prior dispensing devices, enables a respectively low discharge velocity and, therefore, a slow spray 3 with slow propagation velocity.

Preferably, the storage chamber 10 forms a mixing chamber for mixing the gas with the powder. The chamber 10 is preferably designed such that the gas can generate swirls or eddies for better mixing the powder with the gas. Preferably, the chamber 10 is substantially circular in cross section, in particular cylindrical. However, other shapes are also possible.

Further, the chamber 10 is formed with no sharp edges, corners or the like, but has a smooth contour so that the gas can sweep all chamber surfaces to prevent powder accumulating on said surfaces and to ensure or allow complete discharge of the powder. In particular, the gas inlet formed by the piercing element 17 or any other supply element is located opposite to the outlet, i.e., duct 12 and/or nozzle 13, with regard to the axial or outlet direction.

During the dispensing operation, the spray 3 is preferably directly or only generated by the respective insert 6 or its duct 12/nozzle arrangement 13 and output into a mouthpiece 24 of the dispensing device 1 as shown in FIG. 1 for inhalation by a patient or user (not shown).

After dispensing one dose or before or for dispensing the next dose, the piercing element 17 will be withdrawn from the connected insert 6. Preferably, the respective insert 6 is also retracted or pushed back into its cavity 7.

Then, the carrier 5 will be indexed one step further or to the next insert 6, in particular rotated by means of an indexing or transport mechanism (not shown). This mechanism is preferably operated by actuating actuator 19 or any other actuator, by opening a cap or cover of the dispensing device 1 or the like, as already mentioned.

It is noted, that the present invention, in particular the dispensing device 1 and/or the storage device 4, can be used for dispensing one drug, a blend of drugs or at least two or three separate drugs. In the latter case, the separate drugs are stored in separate storage chambers 10, and during the dispensing operation, the drugs are mixed with the gas either in a common mixing chamber or in their respective storage chambers 10. Further, the separate drugs can be discharged through a common duct 12 or nozzle arrangement 13 or through separate ducts 12 or nozzles 13. In the latter case, the separate drugs will be mixed after leaving the separate ducts 12/nozzles 13 or in the mouthpiece 24 or in any other suitable (additional) mixing chamber. It is also possible to mix the separate drugs by impinging jets of the separate drugs. For dispensing the separate drugs, it is preferred to use a common gas supply or means for pressurizing gas such as air pump 18.

Preferably, the spray 3 has a mean velocity (taken 20 cm from the outlet 15 or mouthpiece 24) of less than 2 m/s, in particular less than 1 m/s. Preferably, the mean duration of the spray 3 is at least 0.2 or 0.3 s, and in particular, about 0.5 to 25.

In the preferred embodiment according to FIG. 1, the cavities 7 are orientated in a tangential or radial direction of the storage device 4 or carrier 5. Consequently, the inserts 6 can be individually moved in a tangential or radial direction, in particular, outwardly, in order to open the respective outer seal 9 for dispensing the respective dose of the formulation 2 as indicated in FIG. 1. Accordingly, the mechanism 20 preferably operates in a radial direction for connecting the inserts 6 individually to a gas supply and for pushing the inserts 6 individually at least partially out of the respective cavity 7 and/or through the respective seal 9. This radial movement allows a very compact design of the dispensing device 1, in particular in axial direction.

Preferably, the mouthpiece 24 and the dispensing direction extends in a radial or tangential direction as shown in FIG. 1.

Preferably, the dispensing device 1 comprises a lever or handle (not shown) or the actuator 19 or any other driving or an actuation means for preferably manual actuation in order to index the carrier 5 one step further, i.e., to the next insert 6, and/or to operate the mechanism 20, preferably to connect the respective insert 6 to the gas supply and/or to move/push the respective insert 6 and/or to open the respective seal 9 for dispensing the respective dose of the formulation 2.

It is noted that the dispensing device 1 operates preferably only mechanically.

According to another embodiment (not shown), the inserts 6 may be formed as capsules or the like without any duct 12, nozzle 13 or the like. Instead, each insert 6 is connected individually to a gas supply and to a common outlet arrangement, such as a duct 12, nozzle 13 or the like for dispensing the respective dose of the formulation 2.

According to another embodiment, a secondary packaging may be used for packing and protecting the storage device 4/carrier 5, in particular, for storage purposes before inserting the storage device 4/carrier 5 into the dispensing device 1. Additionally the whole device 1 including the storage device 4/carrier 5 may be stored in a secondary water vapor proof packaging.

According to a further embodiment, the dispensing devise 1 may be breath activated, in particular, wherein the formulation 2 is only released after the patient's or user's inhalation rate has reached a predetermined level, preferably by the use of a pressure sensitive means, such as a bursting element, membrane or valve, or any other mechanism.

According to another embodiment, the dispensing device 1 may also be a passive inhaler wherein a patient or user (not shown) produces an airflow through the respectively opened insert 6, when breathing in so that this airflow entrains the formulation 2 and forms the desired spray 3 in the mouthpiece 24 for inhalation by the patient/user.

It is noted that the term "dispensing device" is to be understood in a broad sense to include other discharge devices, dispensers or the like, preferably, wherein the formulation 2 or any other fluid is sprayed or atomized only when needed, in particularly discontinuously.

In the following, a further preferred embodiment of the dispensing device 1 will be explained with reference to the further drawings. The following description will focus on relevant differences between the further embodiment and the previous embodiments. In particular, the previous explanations and descriptions apply accordingly and/or additionally, even if not repeated.

Figure 7:
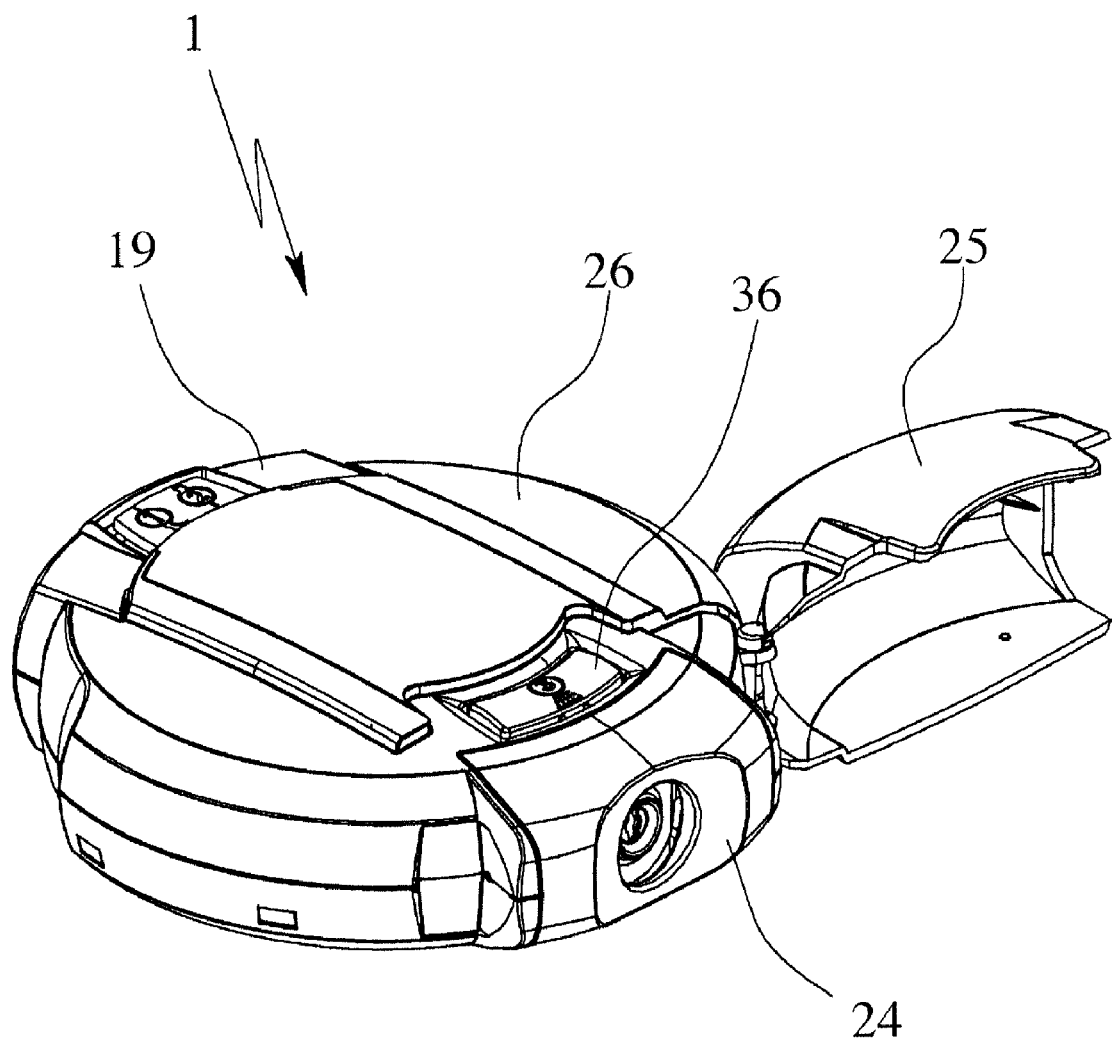

FIG. 7 shows the further embodiment of the dispensing device 1 in a perspective view. The dispensing device 1 comprises a cover 25 for covering the mouthpiece 24. Preferably, the cover 25 mounted so as to pivot for opening or uncovering the mouthpiece 24 as shown. Preferably, the mouthpiece 24 is snapped onto a housing 26 of the dispensing device 1.

The dispensing device 1 comprises an actuator 19 at one side of housing 26, preferably on the side opposite the mouthpiece 24 and/or opposite the main spray direction (preferably in radial direction) of the dispensing device 1. The actuator 19 preferably forms a grip or handle. Therefore, the term "grip" will be used in the following.

The grip 19 is preferably moveable in a radial direction for actuating the dispensing device 1 as explained later in more detail. In particular, the grip 19 can be pulled radially outwardly from the initial position shown in FIG. 7 and pushed back into its initial position. These operations are, for convenience, named "pulling" and "pushing," respectively, in the following. However, it is noted that these operational movements could also be realized by any other direction or type of movement, such as a non-translational movement.

Figure 8:
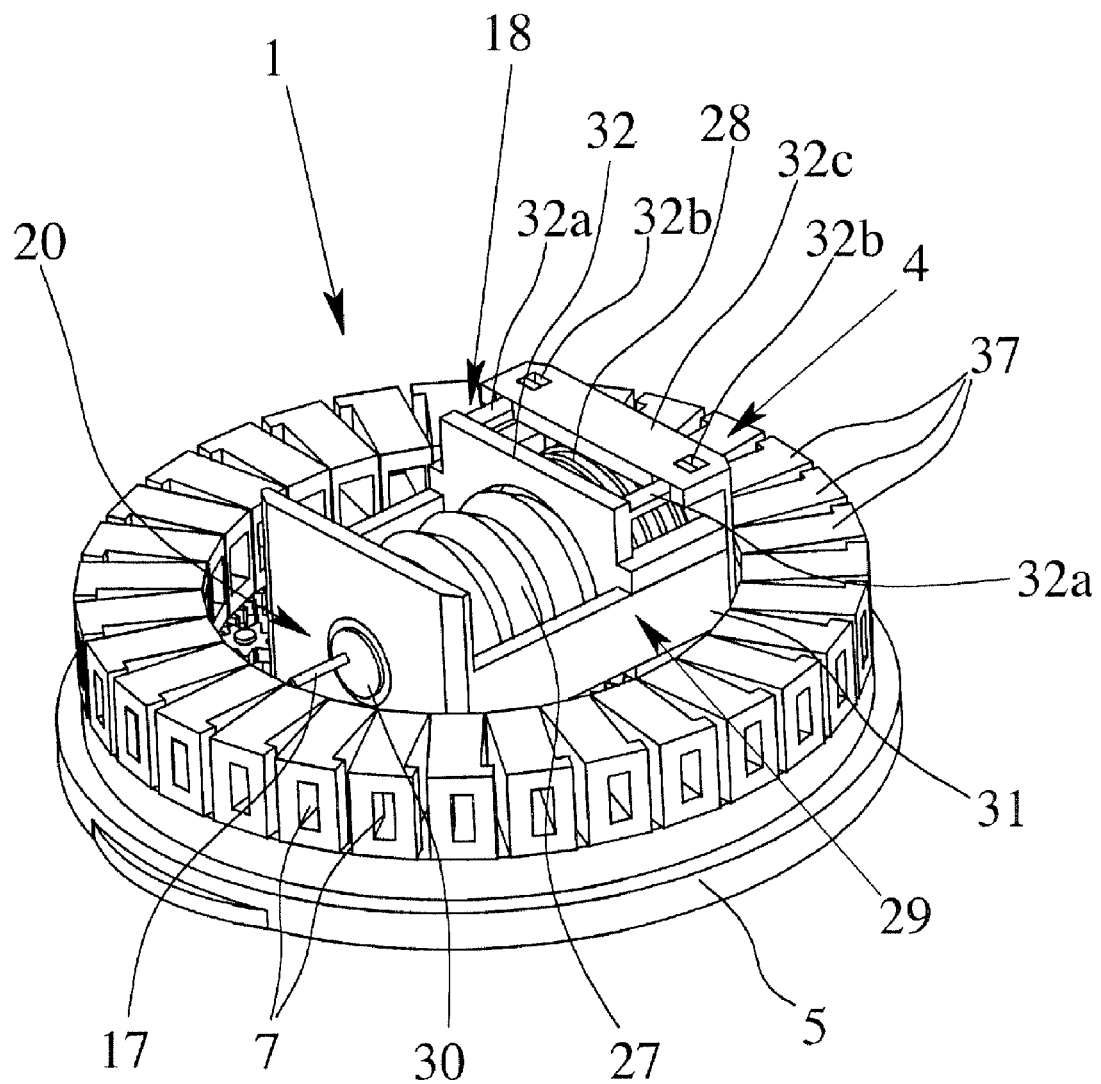
Figure 9:
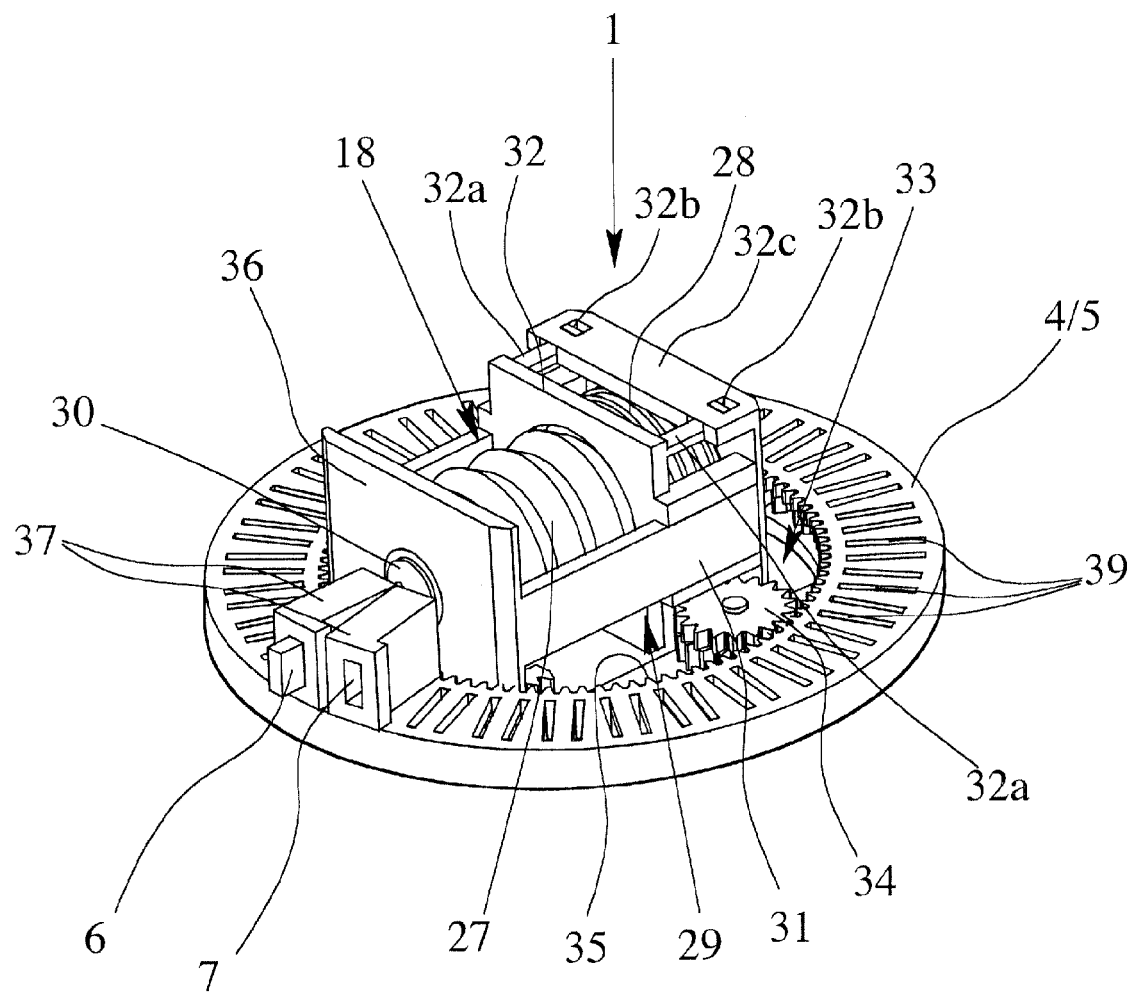
Figure 10:
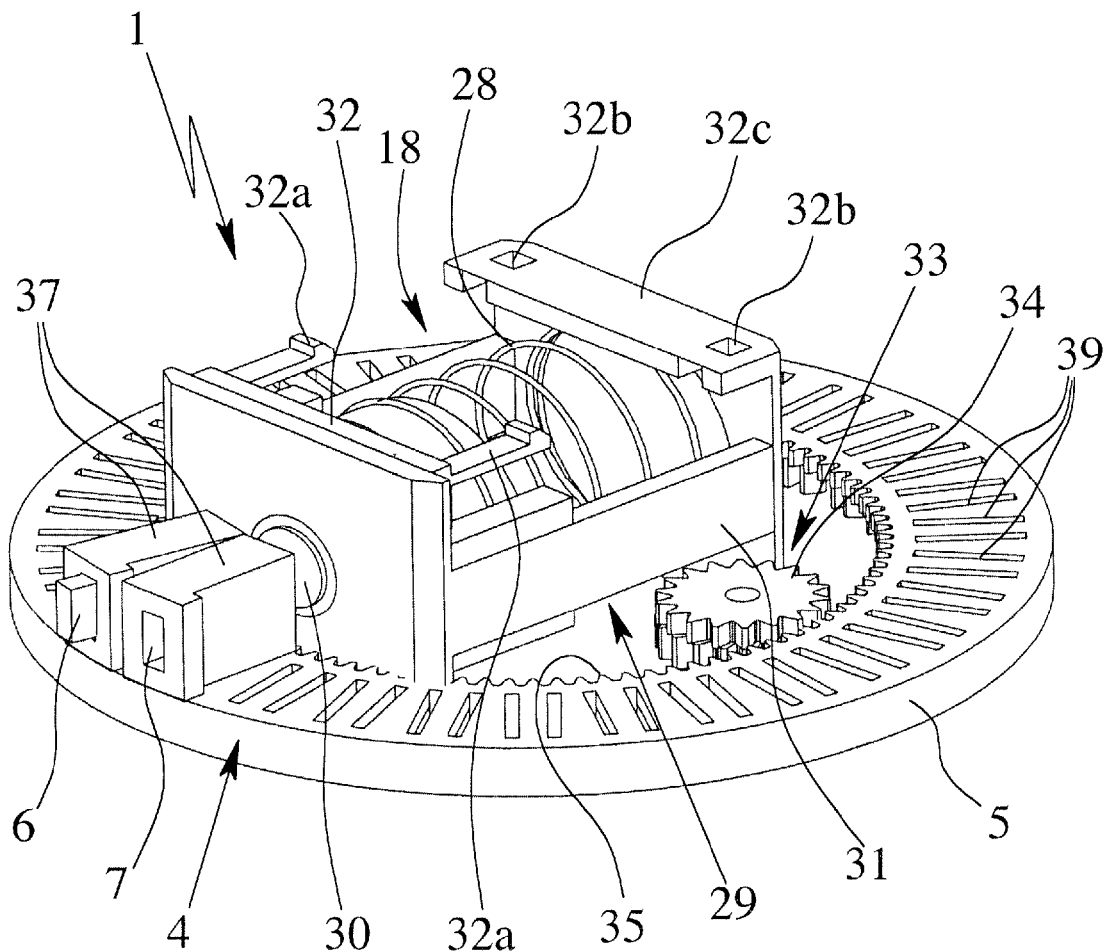

First of all, the basic principle of the dispensing device 1 will be explained with reference to FIGS. 8 to 10. FIGS. 8 to 10 show only very rudimentary schematic views (not to scale) of inner components of the dispensing device 1 for explaining the principle. In particular, the housing 26 and the grip 19 have been omitted. Further, the storage device 4 is shown only in a schematic manner, in particular, incompletely or partially only in FIGS. 9 & 10. In particular, multiple details, such as seals 9, outlets 15 or the like, have been omitted. The preferred construction of the storage device 4 will be explained later after explaining the basic functional principle of the present dispensing device 1.

The dispensing device 1 is an active atomizer or inhaler. The means for pressurizing gas is preferably also constructed as air pump 18. Here, the air pump 18 comprises a bellows 27 as pumping element. However, any other suitable pumping element could be used.

The dispensing device 1/air pump 18 further comprises an energy or spring store, in particular, a spring 28, for actuating the pumping element, i.e., the bellows 27.

The air pump 18 (bellows 27 and spring 28) is preferably radially moveable, in particular, in a sliding manner, such as like a sled. Preferably, the air pump 18 is formed as a slider 29 or is supported thereon. In particular, the air pump 18 and slider 29 will be named the "air assembly" in the following.

Preferably, the air assembly forms or includes the mechanism 20 already mentioned with respect to the previous embodiments. For this purpose, the air assembly preferably comprises a needle holder 30 holding the piercing element/ needle 17. The piercing element 17 may be pressed and/or glued or molded into the needle holder 30. Preferably, the bellows 27 is pressed or clamped onto the needle holder 30.

The needle holder 30 may be designed such that it can push the respective inserts 6 outwardly in case that the sleeve 21 or any other abutment fails.

The needle holder 4 preferably closes or completes the slider frame 31. For example, the needle holder 30 may comprise holds for pins of the slider frame 31, which pins may be heatriveted.

The needle holder 30 is connected to or formed by a slider frame 31, which, in turn, holds the spring 28 and/or moveably guides a tension element 32 associated to the bellows 27 and/or spring 28.

In the illustrated embodiment, the bellows 27 is arranged between the needle holder 30 and the tension element 32. The spring 28 is arranged behind the bellows 27, e.g., on the opposite side of the tension element 32.

The tension element 32 holds the bellows 27 in order to secure the filling of the bellows 27 during pulling. Namely, the grip 19 preferably retracts the tension element 32 during pulling.

The air pump 18 or air assembly is preferably located in the center of the dispensing device 1 and/or within the storage device 4 and/or ring-like carrier 5 and/or is preferably radially moveable.

FIG. 8 shows the situation after the grip 19 has been pulled out. The bellows 27 is extended and filled with air. The spring 28 is compressed or tensioned, i.e., the energy store has stored energy. The tension element 32 is retracted and locked in its position to hold the spring 28 in its compressed state. The air assembly/slider 29 is retracted so that the piercing element 27 is retracted from the storage device 4, in particular, so that the storage device 4 can be indexed or moved, in particular rotated.

When the grip 19 is pushed back, preferably a transportation operation and a connecting operation will be performed. In the first phase of the movement of the grip 19, a transport mechanism 33 is actuated. In particular, a cogwheel 34 of the transport mechanism 33 (shown in FIG. 9) at least temporarily meshing with preferably inner teeth 35 of the storage device 4 or carrier 5 is rotated to move or index the storage device 4 by one insert 6 or cavity 7 and/or to the next insert 6 or cavity 7. However, it is noted that this transportation operation could also be performed partly or completely during pulling.

Preferably, after termination of the transportation operation, i.e., during a second phase of pushing, the connecting operation is performed. The air assembly/slider 29 is moved forward and/or radially so that the piercing element 17 connects to the next/aligned insert 6/cavity 7. In particular, the piercing element 17 pierces into the insert 6 to connect to its storage chamber 10. Before, simultaneously and/or subsequently, the insert 6 is moved radially and/or outward and/or pushed through the outer seal 9. As a result, the insert 6/duct 12/outlet 15 is opened. This situation is shown in FIG. 9, wherein the connected and opened insert 6 is protruding radially outwardly from the storage device 4 and/or its cavity 7.

The spring 28 is still biased or compressed. This situation is also named the "activated state." The dispensing device 1 is ready for dispensing the dose of formulation 2 from the opened/protruding inserts 6 shown in FIG. 9.

To initiate delivery (discharge) of the formulation 2 and to generate the spray 3, a release button 36 (shown in FIG. 7) or any other suitable element is actuated, in particular, depressed. Thus, the tension element 32 or its associated locking means is unlocked (preferably by depressing/compressing the elastic snap 32a), and the spring 28 is released and compresses the bellows 27. The bellows 27 compresses the air contained therein. Thus, the air is forced through piercing element 17 into the connected insert 6. The resulting air stream is forced through the connected insert 6, entraining the powder/formulation 2 of the insert 6 and ejecting it as spray 3.

FIG. 10 shows the final state after discharge. The spring 28 has expanded and the bellows 27 compressed. The tension element 32 has been moved forward to the needle holder 30/piercing element 17. The piercing element 17 is still connected to the emptied insert 6, and the emptied insert 6 is still protruding outward. In this state, the dispensing device 1 can be closed and transported. Therefore, this state is also named the "transportation state."

For the next use, the grip 19 is pulled. In a first phase of the movement, the slider 29/air assembly is retracted together with the piercing element 17 so that the piercing element 17 is retracted from the storage device 4, i.e., out of the cavity 7 of the last insert 6. In a second phase of movement, which can also happen simultaneously, but is preferably performed after the slider 29 has stopped, the tension element 32 is retracted within the slider 29/slider frame 31 so that the bellows 27 is extended and the spring 28 is compressed or biased until the tension element 32 is locked in its retracted position as shown in FIG. 8. During the extension of the bellows 27, air is sucked into the bellows 27, preferably through piercing element 17 and/or optionally through a suitable inlet valve (not shown).

It is noted that the release button 36 is preferably lifted only during the last phase of pushing the grip 19. Further, the lifted or activated or primed release button 36 preferably blocks pulling of the grip 19 until the release button 36 has been actuated or depressed, i.e., until the dispensing device 1 has been triggered. In particular, the release button 36 is tilted during actuation or depressing.

In the following, further details, aspects, features and advantages of the present dispensing device 1 and/or of its components will be explained.

Preferably, the storage device 4 comprises multiple receptacles 37 respectively containing only or at least one insert 6, as schematically shown in FIGS. 8 to 10. In particular, the receptacles 37 are produced as separate parts that are placed or mounted on the carrier 5.

The receptacles 37 may be made of the same material as the storage device 4/carrier 5, in particular of plastic. Preferably, the receptacles 37 are rigid and form a guide for the inserts 6.

Each of the receptacles 37 comprises one or more cavities 7 for receiving the respective insert(s) 6.

Preferably, the receptacles 37 are provided with the inserts 6 already filled with the respective dose of formulation 2, and then, mounted on the comment carrier 5.

The receptacles 37 are preferably sealed separately, i.e., independently from each other and/or with separate seals 9. The receptacles 37 may be sealed before or after placement on the carrier 5. The receptacles 37 are preferably sealed on opposite sides and/or on longitudinal end faces.

Figure 11:
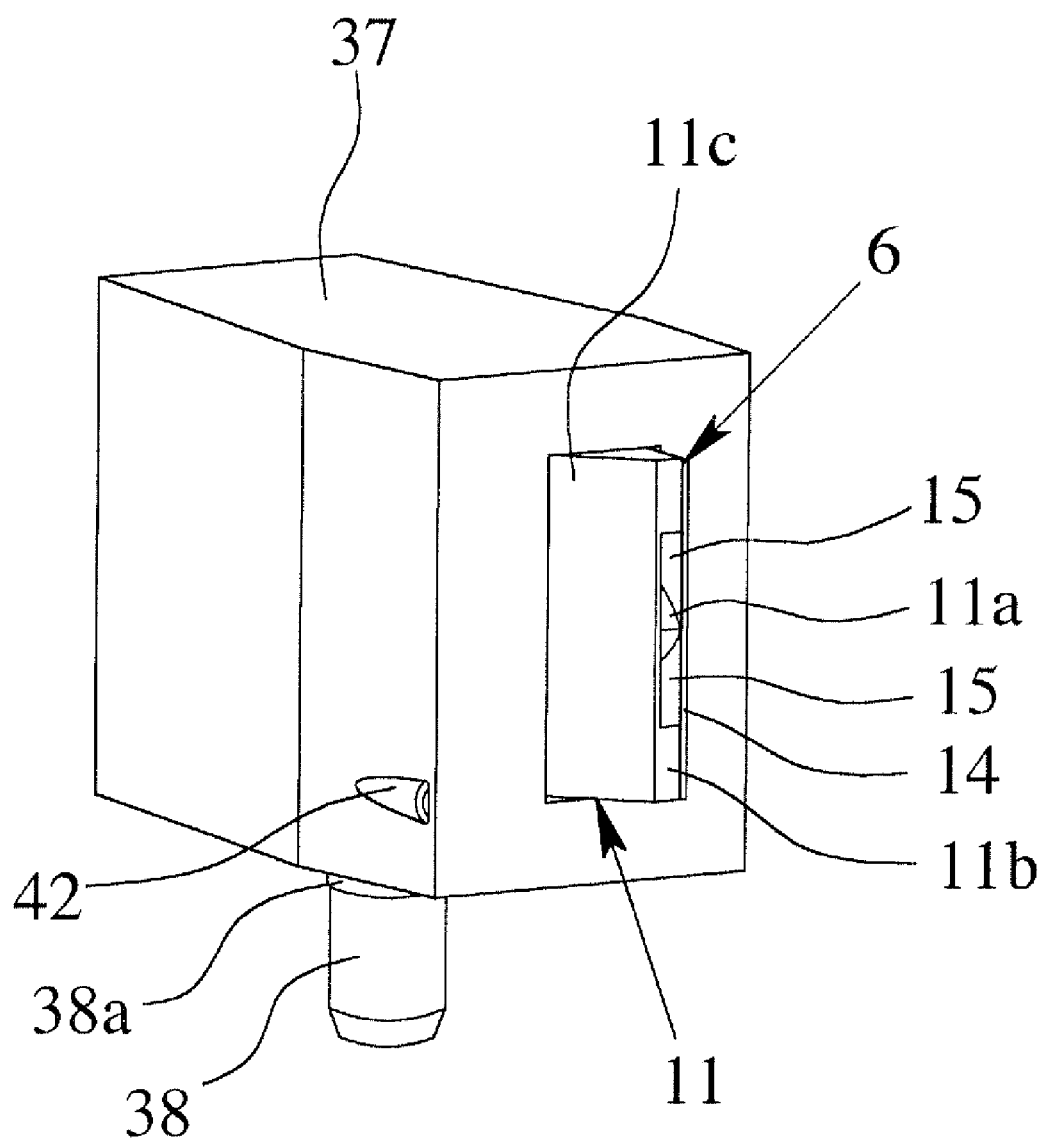

FIG. 11 shows in a schematic perspective view one receptacle 37 before placement on the carrier 5. Preferably, the receptacle 37 has an essentially cuboid and/or longitudinal form.

The carrier 5 preferably supports the receptacles 37 fixedly and/or in a form-fit manner. Preferably, the receptacles 37 are snapped on to or into the carrier 5.

Figure 12:
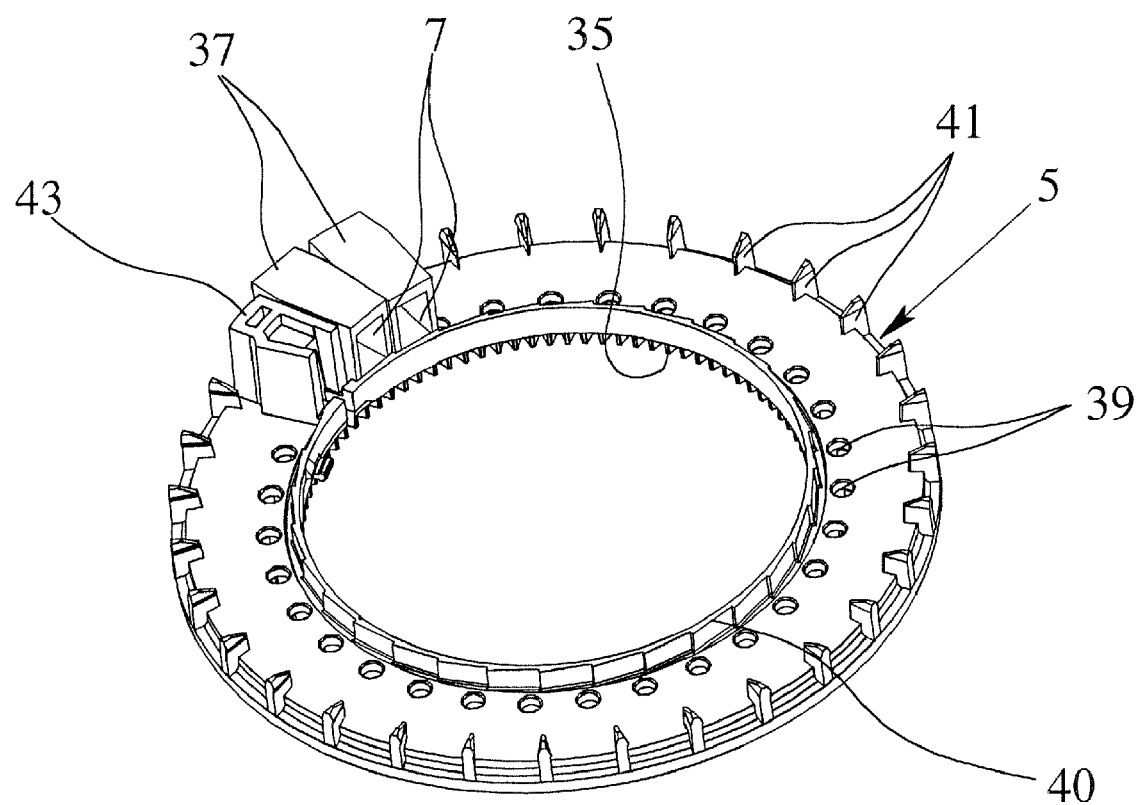

In the present embodiment, the receptacles 37 comprise a protrusion 38 for mounting the respective receptacle 37 onto carrier 5. The carrier 5 comprises a series of corresponding recesses 39, such as slits or grooves, as shown in FIGS. 9 & 10. In the embodiment shown in FIG. 11, there are bores for receiving the protrusions 38. In particular, the receptacles 37 can be snapped, clipped, clamped or pressed with their protrusions 38 into the recesses 39 of the carrier 5. For this purpose, the protrusions 38 may comprise a preferably annular portion 38a with increased diameter or the like. FIG. 12 shows in a schematic perspective view a preferred embodiment of the carrier 5 with bores being provided as recesses 39. Preferably, the recesses and/or protrusions 38 are arranged adjacent to the inner surfaces of the storage device 4, to the inner openings 8 and/or to the side at which piercing or pushing of the respective inserts 6 occurs. However, other mechanical solutions or designs are possible to connect the receptacles 37 with the carrier 5.

Alternatively or in additional to the recesses or bores 39, the carrier 5 may comprise means for fixing and/or aligning the receptacles 37 on the carrier 5. In the illustrated embodiment, the carrier 5 preferably comprises an inner ring wall 40 and/or holding elements 41.

The inner ring wall 40 may form an abutment or stop for the inserts 6 which prevent the inserts 6 from being pulled out of their cavities 7 when retracting the piercing element 17.

The holding elements 41 are preferably located at the periphery of the carrier 5 and protrude preferably upwardly so that each receptacle 37 can be placed between two adjacent holding elements 41. In particular, the holding elements 41 align the receptacles 37 on the carrier 5 correctly and/or radially.

Preferably, the receptacles 37 can be snapped or clamped between adjacent holding elements 41. For this purpose, the receptacles 37 may comprise noses 42 or other suitable engaging means on its respective sides which can be engaged or hooked by the preferably flexible and/or arm-like holding elements 41. Thus, it is possible to hold or fix the receptacles 37 at its outer periphery and/or such that any tilting can be avoided, even when the piercing element 17 is retracted.

It is noted that the carrier 5 preferably comprises a "dummy" receptacle 43 without any insert 6 for receiving the piercing element 17 in the initial transportation state (delivery state) of the dispensing device 1, i.e., before first use of the dispensing device 1, wherein the assembly is in the position shown in FIG. 10, but the piercing element 17 extends into the dummy receptacle 43.

Figure 13:
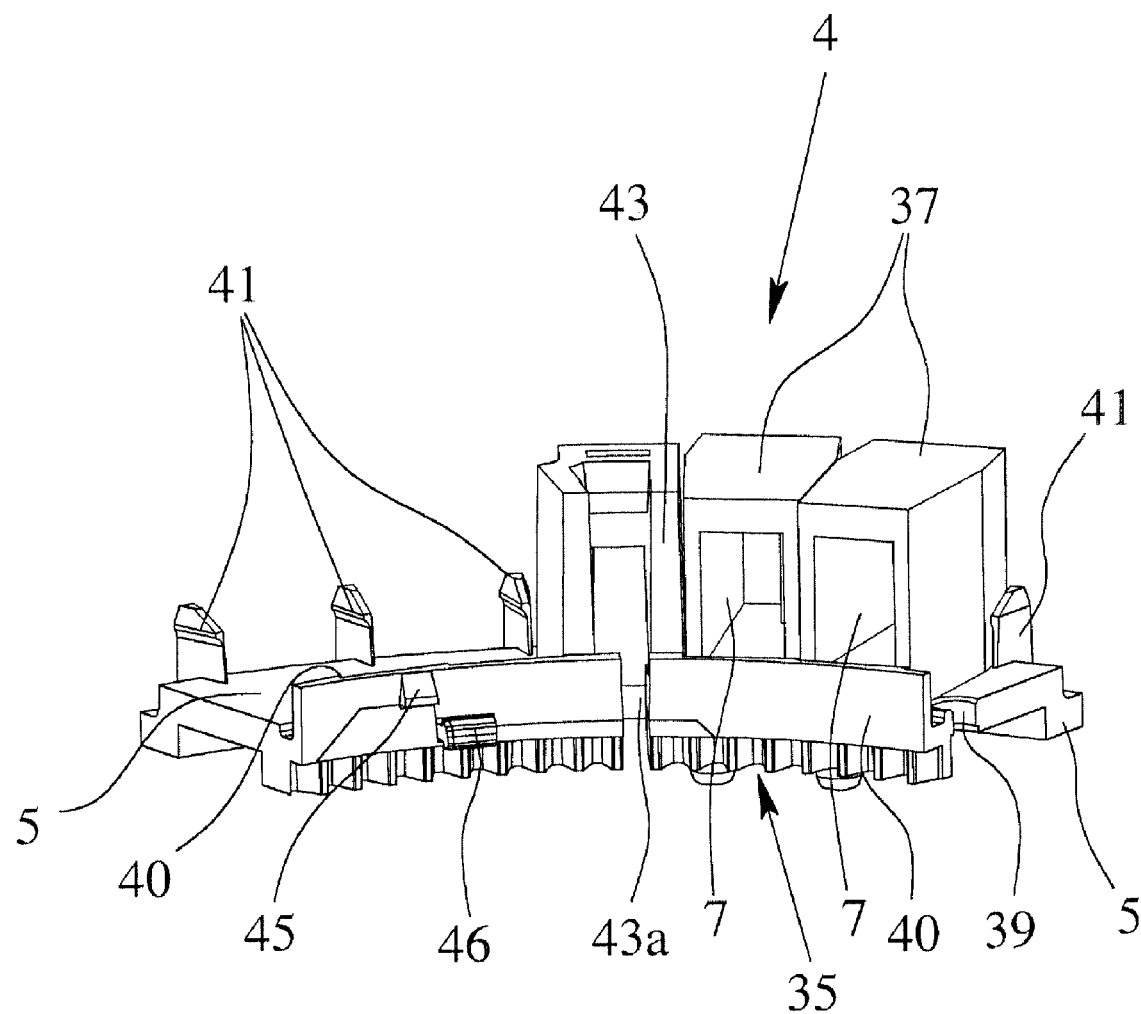

FIG. 13 shows in a partial, enlarged view of the carrier 5, the preferably hollow dummy receptacle 43. In particular, the dummy receptacle 43 is axially open at one side (slit 43a)

and/or is radially open at its inner side so that the piercing element 17 can be axially inserted when mounting the dispensing device 1.

Further, FIG. 13 shows that the holding elements 41 are preferably provided with undercuts or transversely extending portions at their free ends or other suitable means to surely hold the receptacles 37 between the holding elements 41 by engaging the noses 42.

Figure 14:
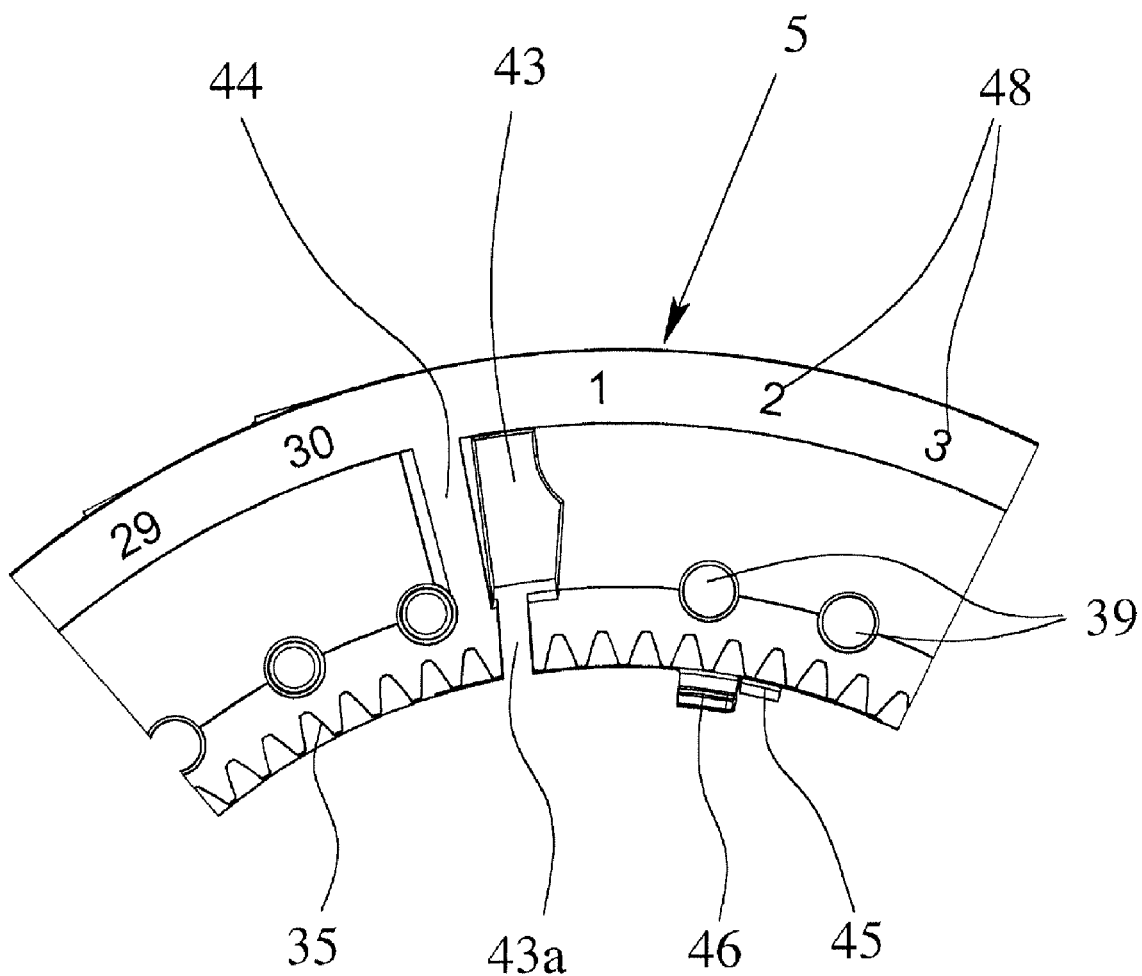

FIG. 14 shows a partial, enlarged view of the carrier 5 from the other side.

The dispensing device 1 comprises preferably a lifespan block (LSB). After using or operating the dispensing device 1 for the predetermined number of uses (number of doses or inserts 6), in the present embodiment e.g., 30 applications, the dispensing device 1 is locked up completely in order to avoid any further inadvertent applications. Preferably, the dispensing device 1 has multiple independently working LSB locks. In particular, the locks are unlockable and/or lock by form-fit.

The first LSB lock may be formed by an abutment, such as a rib 44 as shown in FIG. 14 or the like, on the storage device 4 or its carrier 5. The abutment limits the rotation of the storage device 4/carrier 5 in that it abuts at a respective stop provided by the housing 26 or any other suitable, in particular rigid or stationary part of the dispensing device 1 when the last insert 6/cavity 7 has been aligned with respect to the air assembly or piercing element 17.

A second LSB lock may be formed by a snap nose 45 formed on the storage device 4, in particular, the carrier 5 as shown in FIG. 13, for locking the release button 36 in its actuated or depressed position after the last use of the dispensing device 1. Thus, any further triggering or any further pump operation would be prevented.

A third LSB lock may be formed by a snap hook 46 also provided on the storage device 4, in particular, the carrier 5, for locking the grip 19 in the inner or pushed position (as shown in FIG. 7) when the storage device 4/carrier 5 has reached its end position and the storage device 4/carrier 5 has reached its last position/receptacle 37. In particular, the grip 19 may hook with one holding arm or two holding arms 57 (shown in FIG. 16) to the snap hook 46 in the locked state.

Preferably, the LSB locks described above and/or any other LSB locks do not require any additional component. In the preferred embodiment, the dispensing device 1 does not require any additional components for forming one, multiple or all LSB locks as described above and/or of any other type.

It is noted that the different LSB locks described above can be used in any combination with each other and/or with other LSB locks. Further, the LSB locks described above can also be used independently of each other in the present dispensing device 1 or in any other dispensing device 1.

locking of the grip 19 against pulling. In particular, the grip 19 has to be decoupled before it can be pulled. In the present embodiment, the decoupling can be achieved by Preferably, the storage device 4/carrier 5/receptacles 37 interact with the air assembly/slider 29 such that a correct alignment of the piercing element 17 and the respective receptacle 37 or insert 6 is ensured before the piercing element 17 pierces or opens the respective receptacle 37, cavity 7 and/or insert 6. For this purpose, the air assembly or slider 29 preferably comprises an engagement portion, in particular, a fork portion 47 (FIG. 15), which interacts with the storage device 4, carrier 5 and/or the respective receptacle 37 to achieve the desired (fine) alignment.

Figure 15:
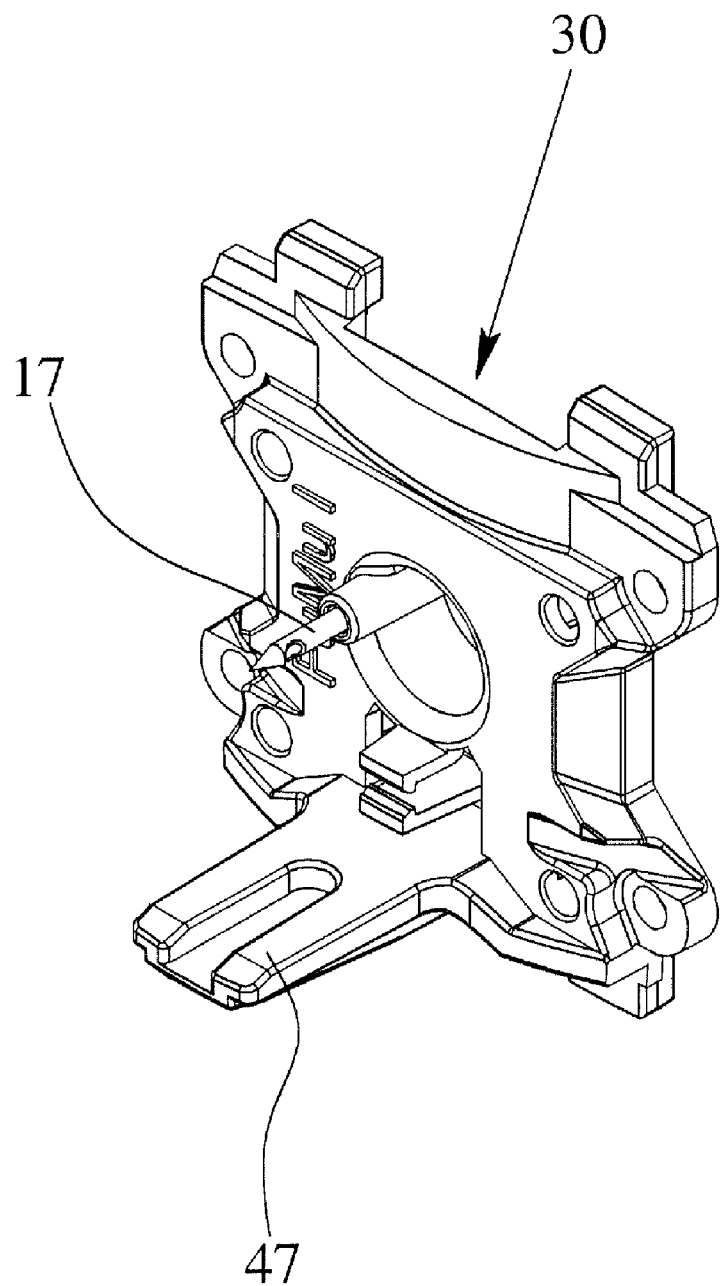

In the present embodiment, the engagement portion or fork portion 47 protrudes from the air assembly, in particular, from the needle holder 30, which is shown in detail in FIG. 15. The engagement portion or fork portion 47 preferably interacts with alignment means or guiding portions associated to each insert 6. In the present embodiment, these alignment means or guiding portions are preferably formed by the protrusions 38, which protrude through the recesses 39 and extend outwardly or axially from the carrier 5. Thus, a direct and optimized (fine) alignment can be positively achieved between the piercing element 17 and the respective insert 6 with minimal tolerances.

Preferably, the inserts 6 are restricted in their backward movement as already mentioned so that the piercing element 17 can be retracted and uncoupled from the respective insert in a definitive manner when the air assembly/slider 29 is retracted into the position shown in FIG. 8. This restriction or limitation is preferably achieved by a respective stop or abutment at the storage device 4 or carrier 5. In particular, this stop or abutment is formed by the inner ring wall 40 or any other suitable means.

The dispensing device 1 comprises preferably a counter for counting or showing the used or unused doses or operations. Preferably, the counter device is formed by a numbering 48 on the storage device 4, in particular on the carrier 5 as shown in FIG. 14. The numbering 48 is visible through a respective window or transparent portion (not shown) of the housing 26.

Figure 16:
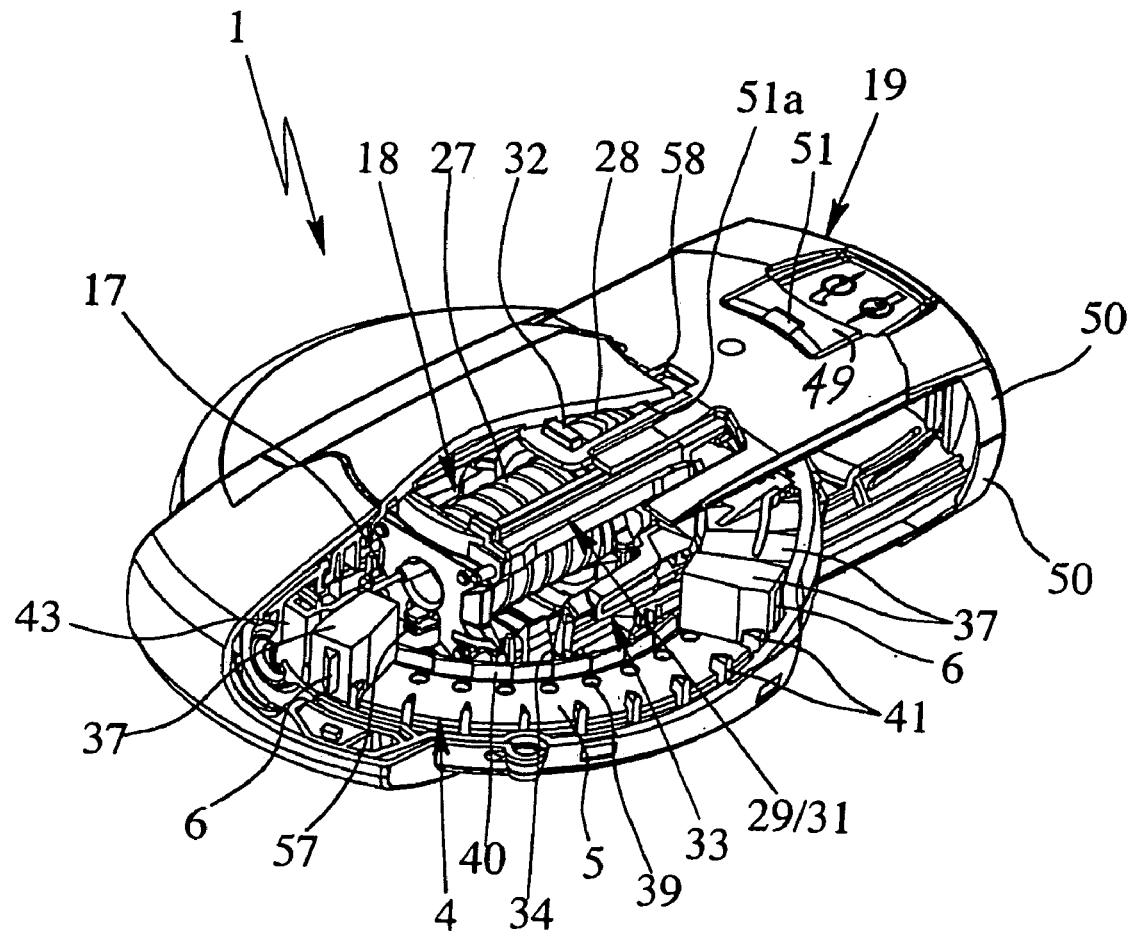

The dispensing device 1 preferably comprises a means for preventing a back stroke of the air assembly, in particular, of the piercing element 17, when discharge of a dose of formulation 2 is triggered (by actuating release button 36) and the spring 28 moves forward and the gas or air is forced through the respective insert 6. Preferably, this means is realized by respective depressing a portion 49 of the grip 19, in particular by pressing opposite portions 49 of the grip 19 together so that a respective undercut or snap engagement between the grip 19 and the housing 26 can be unlocked. In particular, the grip 19 consists of two grip parts or halves 50 as shown in FIG. 16. Preferably, each half 50 comprises a flexible or depressible portion 49 with an associated snap portion 51. The snap portion can engage into a recess or undercut 51a formed in the housing 26 as schematically shown in FIG. 16 to lock the grip 19 in the pushed position (FIG. 16 shows the grip 19 in the pulled position).

Figure 17:
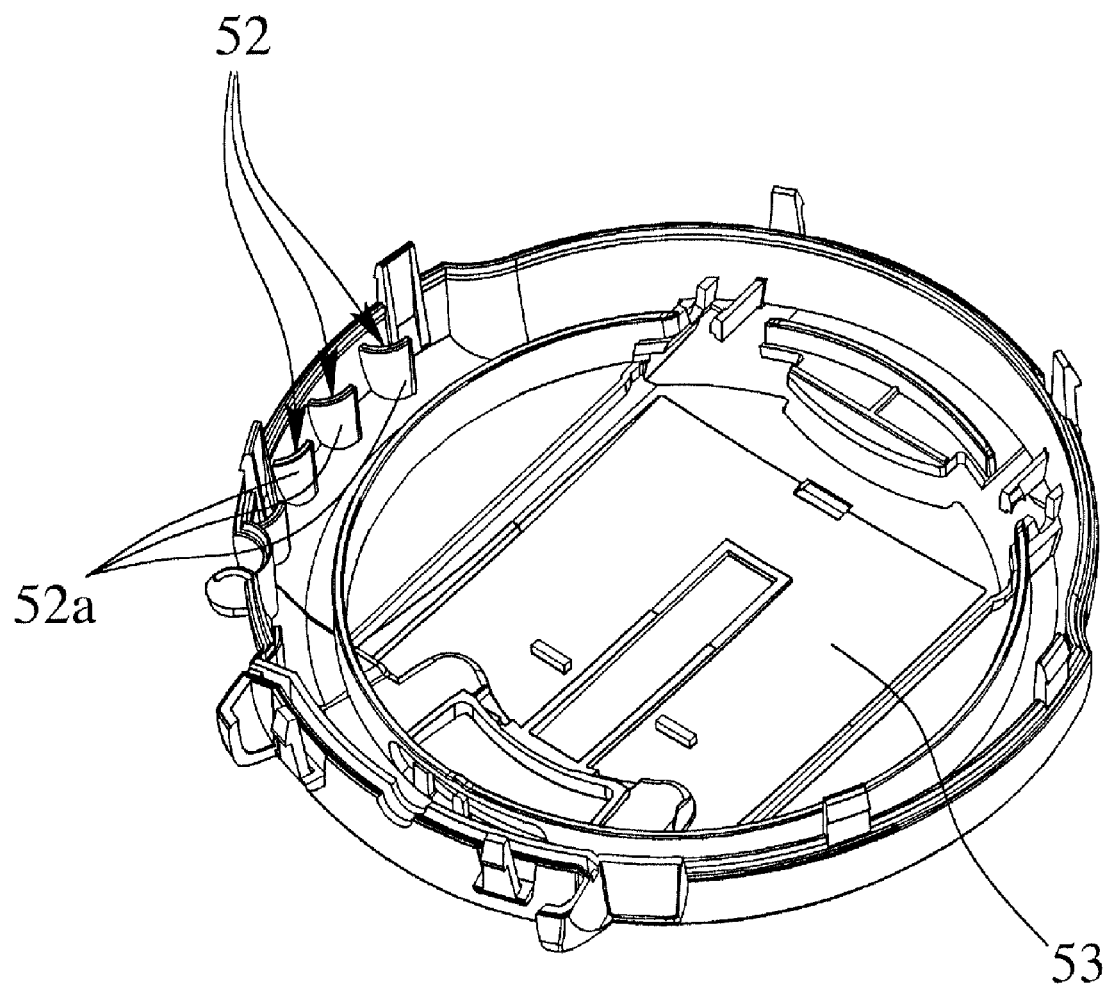

The dispensing device 1 comprises preferably a means for moving or pressing the used inserts 6 back into their respective cavities 7 or receptacles 37. This means preferably comprises at least one preferably stationary and/or rigid guiding element 52, here, multiple rib-like guiding elements 52 are arranged inside the housing 26 adjacent to the outer periphery of the storage device 4 and after the mouthpiece 24, in particular on or in one half 53 of the housing 26 as shown in FIG. 17. Due to the relative movement of the storage device 4 and the housing 26 or guiding elements 52, inclined surfaces 52a of the guiding elements 52 press or push the used insert 6 back into the storage device 4 or its respective cavity 7 or receptacle 37, preferably in multiple steps. Alternatively or additionally the inclined portions 11c of the inserts 6 may be used to move, press or urge the used inserts 6 back into their cavities 7, in particular, in cooperation with a preferably stationary guiding element 52 or the like.

In the present embodiment, a locking means is provided for locking the tension element 32 in the retracted position. Here, the locking means comprises at least one snap hook or arm 32a, preferably two or more snap arms 32a, that engage into respective undercuts, recesses or snap openings 32b that are preferably formed by or in a back shield 32c of the slider 29 or slider frame 31 or vice versa. However, other constructional solutions are possible.

The dispensing device 1 is preferably an active powder inhaler, i.e., the powder is discharged by pressurized gas, in particular air. Nevertheless, the dispensing operation may be triggered by the inhalation or breathing in of a patient. In particular, the dispensing device 1 comprises detection means for detecting inhalation or breathing in by the user and/or trigger means for triggering dispensing of the respective dose.

Preferably, the detection means comprises a sensor 55 (FIG. 1) for detecting at least one of a pressure, a pressure drop, a velocity, an increase of velocity or any associated value thereof of the air flowing through the dispensing device, in particular, through the mouthpiece 24, when a patient breathes in. The respective detection signal indicating breathing in by a patient may be used by the trigger means in order to trigger dispensing of the respective dose by means of pressurized gas. In particular, the trigger means comprises a controller 54 and/or a valve 56 associated with the means for pressurizing gas, in particular the air pump 18, a gas supply line, the piercing element 17 or the like controls or triggers the flow of pressurized gas to and through the respective storage chamber 10 or the like for dispensing the respective dose of formulation 2.

Preferably, the trigger means operates electrically, electronically, pneumatically or mechanically. For example, the detection means and trigger means may be formed by an appropriate valve 65 that opens the supply of pressurized gas through the respective receptacle 37, insert 6 and/or storage chamber 10 when the pressure in the mouthpiece 24 drops due to breathing in of a patient. Then, the valve 56 preferably stays open until the flow of pressurized gas stops or the gas pressure reaches or drops bellow an appropriate pressure limit. Such a functionality may be realized without using electric or electronic components.

There are multiple other mechanisms possible. According to another embodiment, a sealed outer case can have a flexible diaphragm, e.g., made of rubber, mounted within its wall with one surface facing the inside and the other exposed to atmosphere. A linkage with mechanical advantage (amplification) connects the diaphragm to the tension element 32 (FIGS. 8 & 9) or to the valve 56 or any other suitable means to control gas supply. When the user or patient inhales via the mouthpiece 24, the sealed case ensures a pressure reduction due to which the diaphragm bends into the case activating or acting on the mechanical link, and thus, triggers dispensing, in particular, by releasing tension element 32, opening valve 56 or the like.

According to another embodiment, a flap can be sealingly positioned within the mouthpiece 24 and connected to the tension element 32, the valve 56 or the like via a linkage with mechanical advantage or amplification. When the user or patient inhales, the air flow/pressure difference opens or actuates the flap activating or operating the link, and thus, triggers dispensing, in particular, by releasing tension element 32, opening valve 56 or the like.

According to another embodiment, an electronic system can be used. A pressure sensitive actuator can be connected to tension element 32 so that tension element 32 can be released when detecting inhalation or breathing in of a user or patient.

Preferably, the automatic triggering or dispensing is only possible when the dispensing device 1 has been activated and/or dispensing has been allowed, in particular, by actuating the release button 36 or any other actuator, before the trigger means may eventually trigger the dispensing when breathing in is detected.

Preferably, the grip 19 and the tension element 32 interact directly or indirectly such that the tension element 32 can be moved by pulling the grip 19 to compress the spring 28, but can move back into the position with decompressed spring 28 without movement of grip 19 when triggering dispensing. For this purpose, the tension element 32 engages preferably into a slit portion 58 formed, in particular, by grip 19.

Preferably, the insert 6, the cavities 7 and/or the receptacles 37 are annually arranged. However, any other arrangement, in particular a linear arrangement or the like, is also possible.

In particular, the dispensing device 1 is a preferably oral and/or active inhaler, a hand-held device and/or preferably only manually operated. Most preferably, the dispensing device 1 is a dry powder inhaler.

Individual features and aspects of the individual embodiments may also be combined with one another as desired or used in other constructions of atomizers, inhalers, dispensers or the like.

Some preferred ingredients and/or compositions of the preferably medicinal formulation 2 are listed below. As already mentioned, they are in particular powders or liquids in the broadest sense. Particularly preferably the formulation 2 contains the following:

The compounds listed below may be used in the device according to the invention on their own or in combination. In the compounds mentioned below, W is a pharmacologically active substance and is selected (for example) from among the betamimetics, anticholinergics, corticosteroids, PDE4-inhibitors, LTD4-antagonists, EGFR-inhibitors, dopamine agonists, H1-antihistamines, PAF-antagonists and PI3-kinase inhibitors. Moreover, double or triple combinations of W may be combined and used in the device according to the invention. Combinations of W might be, for example:

- W denotes a betamimetic, combined with an anticholinergic, corticosteroid, PDE4-inhibitor, EGFR-inhibitor or LTD4-antagonist,
- W denotes an anticholinergic, combined with a betamimetic, corticosteroid, PDE4-inhibitor, EGFR-inhibitor or LTD4-antagonist,
- W denotes a corticosteroid, combined with a PDE4-inhibitor, EGFR-inhibitor or LTD4-antagonist
- W denotes a PDE4-inhibitor, combined with an EGFR-inhibitor or LTD4-antagonist
- W denotes an EGFR-inhibitor, combined with an LTD4-antagonist.

The compounds used as betamimetics are preferably compounds selected from among albuterol, arformoterol, bambuterol, bitolterol, broxaterol, carbuterol, clenbuterol, fenoterol, formoterol, hexoprenaline, ibuterol, isoetharine, isoprenaline, levosalbutamol, mabuterol, meluadrine, metaproterenol, orciprenaline, pirbuterol, procaterol, reproterol, rimiterol, ritodrine, salmefamol, salmeterol, soterenol, sulphonterol, terbutaline, tiaramide, tolubuterol, zinterol, CHF-1035, HOKU-81, KUL-1248 and 3-(4-{6-[2-hydroxy-2-(4-hydroxy-3-hydroxymethyl-phenyl)-ethylamino]-hexyloxy}-butyl)-benzyl-sulphonamide 5-[2-(5.6-diethyl-indan-2-ylamino)-1-hydroxy-ethyl]-8-hydroxy-1H-quinolin-2-one 4-hydroxy-7-[2-{[2-{[3-(2-phenylethoxy)propyl]sulphonyl}ethyl]-amino}ethyl]-2(3H)-benzothiazolone 1-(2-fluoro-4-hydroxyphenyl)-2-[4-(1-benzimidazolyl)-2-methyl-2-butylamino]ethanol 1-[3-(4-methoxybenzyl-amino)-4-hydroxyphenyl]-2-[4-(1-benzimidazolyl)-2-methyl-2-butylamino]ethanol 1-[2H-5-hydroxy-3-oxo-4H-1,4-benzoxazin-8-yl]-2-[3-(4-N,N-dimethylaminophenyl)-2-methyl-2-propylamino]ethanol 1-[2H-5-hydroxy-3-oxo-4H-1,4-benzoxazin-8-yl]-2-[3-(4-methoxyphenyl)-2-methyl-2-propylamino]ethanol 1-[2H-5-hydroxy-3-oxo-4H-1,4-benzoxazin-8-yl]-2-[3-(4-n-butyloxyphenyl)-2-methyl-2-propylamino]ethanol 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol
5-hydroxy-8-(1-hydroxy-2-isopropylaminobutyl)-2H-1,4-benzoxazin-3-(4H)-one
1-(4-amino-3-chloro-5-trifluoromethylphenyl)-2-tert.-butylamino)ethanol
6-hydroxy-8-{1-hydroxy-2-[2-(4-methoxy-phenyl)-1,1-dimethyl-ethylamino]-ethyl}-4H-benzo[1,4]oxazin-3-one
6-hydroxy-8-{1-hydroxy-2-[2-(ethyl 4-phenoxy-acetate)-1,1-dimethyl-ethylamino]-ethyl}-4H-benzo[1,4]oxazin-3-one
6-hydroxy-8-{1-hydroxy-2-[2-(4-phenoxy-acetic acid)-1,1-dimethyl-ethylamino]-ethyl}-4H-benzo[1,4]oxazin-3-one
8-{2-[1,1-dimethyl-2-(2.4.6-trimethylphenyl)-ethylamino]-1-hydroxy-ethyl}-6-hydroxy-4H-benzo[1,4]oxazin-3-one
6-hydroxy-8-{1-hydroxy-2-[2-(4-hydroxy-phenyl)-1,1-dimethyl-ethylamino]-ethyl}-4H-benzo[1,4]oxazin-3-one
6-hydroxy-8-{1-hydroxy-2-[2-(4-isopropyl-phenyl)-1.1 dimethyl-ethylamino]-ethyl}-4H-benzo[1,4]oxazin-3-one
8-{2-[2-(4-ethyl-phenyl)-1,1-dimethyl-ethylamino]-1-hydroxy-ethyl}-6-hydroxy-4H-benzo[1,4]oxazin-3-one
8-{2-[2-(4-ethoxy-phenyl)-1,1-dimethyl-ethylamino]-1-hydroxy-ethyl}-6-hydroxy-4H-benzo[1,4]oxazin-3-one
4-(4-{2-[2-hydroxy-2-(6-hydroxy-3-oxo-3,4-dihydro-2H-benzo[1,4]oxazin-8-yl)-ethylamino]-2-methyl-propyl}-phenoxy)-butyric acid
8-{2-[2-(3.4-difluoro-phenyl)-1,1-dimethyl-ethylamino]-1-hydroxy-ethyl}-6-hydroxy-4H-benzo[1,4]oxazin-3-one
1-(4-ethoxy-carbonylamino-3-cyano-5-fluorophenyl)-2-(tert-butylamino)ethanol
2-hydroxy-5-(1-hydroxy-2-{2-[4-(2-hydroxy-2-phenyl-ethylamino)-phenyl]-ethylamino}-ethyl)-benzaldehyde
N-[2-hydroxy-5-(1-hydroxy-2-{2-[4-(2-hydroxy-2-phenyl-ethylamino)-phenyl]-ethylamino}-ethyl)-phenyl]-formamide
8-hydroxy-5-(1-hydroxy-2-{2-[4-(6-methoxy-biphenyl-3-ylamino)-phenyl]-ethylamino}-ethyl)-1H-quinolin-2-one
8-hydroxy-5-[1-hydroxy-2-(6-phenethylamino-hexylamino)-ethyl]-1H-quinolin-2-one
5-[2-(2-{4-[4-(2-amino-2-methyl-propoxy)-phenylamino]-phenyl}-ethylamino)-1-hydroxy-ethyl]-8-hydroxy-1H-quinolin-2-one
[3-(4-{6-[2-hydroxy-2-(4-hydroxy-3-hydroxymethyl-phenyl)-ethylamino]-hexyloxy}-butyl)-5-methyl-phenyl]-urea
4-(2-{6-[2-(2.6-dichloro-benzyloxy)-ethoxy]-hexylamino}-1-hydroxy-ethyl)-2-hydroxymethyl-phenol
3-(4-{6-[2-hydroxy-2-(4-hydroxy-3-hydroxymethyl-phenyl)-ethylamino]-hexyloxy}-butyl)-benzylsulphonamide
3-(3-{7-[2-hydroxy-2-(4-hydroxy-3-hydroxymethyl-phenyl)-ethylamino]-heptyloxy}-propyl)-benzylsulphonamide
4-(2-{6-[4-(3-cyclopentanesulphonyl-phenyl)-butoxy]-hexylamino}-1-hydroxy-ethyl)-2-hydroxymethyl-phenol
N-Adamantan-2-yl-2-(3-{2-[2-hydroxy-2-(4-hydroxy-3-hydroxymethyl-phenyl)-ethylamino]-propyl}-phenyl)-acetamide optionally in the form of the racemates, enantiomers, diastereomers thereof and optionally in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The anticholinergics used are preferably compounds selected from among the tiotropium salts, preferably the bromide salt, oxitropium salts, preferably the bromide salt, flutropium salts, preferably the bromide salt, ipratropium salts, preferably the bromide salt, glycopyrronium salts, preferably the bromide salt, trospium salts, preferably the chloride salt, tolterodine. In the above-mentioned salts the cations are the pharmacologically active constituents. As anions the above-mentioned salts may preferably contain the chloride, bromide, iodide, sulphate, phosphate, methanesulphonate, nitrate, maleate, acetate, citrate, fumarate, tartrate, oxalate, succinate, benzoate or p-toluenesulphonate, while chloride, bromide, iodide, sulphate, methanesulphonate or p-toluenesulphonate are preferred as counter-ions. Of all the salts the chlorides, bromides, iodides and methanesulphonates are particularly preferred.

Other preferred anticholinergics are selected from among the salts of formula AC-1

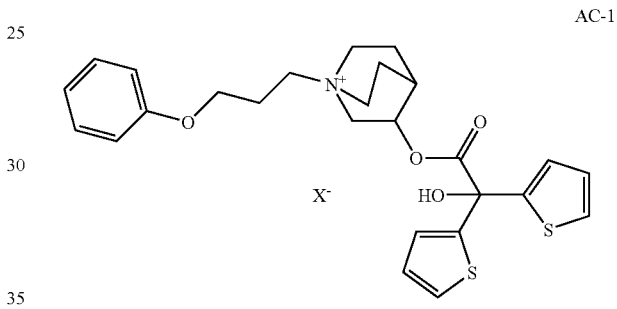

AC-1 wherein $X^-$ denotes an anion with a single negative charge, preferably an anion selected from among the fluoride, chloride, bromide, iodide, sulphate, phosphate, methanesulphonate, nitrate, maleate, acetate, citrate, fumarate, tartrate, oxalate, succinate, benzoate and p-toluenesulphonate, preferably an anion with a single negative charge, particularly preferably an anion selected from among the fluoride, chloride, bromide, methanesulphonate and p-toluenesulphonate, particularly preferably bromide, optionally in the form of the racemates, enantiomers or hydrates thereof. Of particular importance are those pharmaceutical combinations which contain the enantiomers of formula AC-1-en

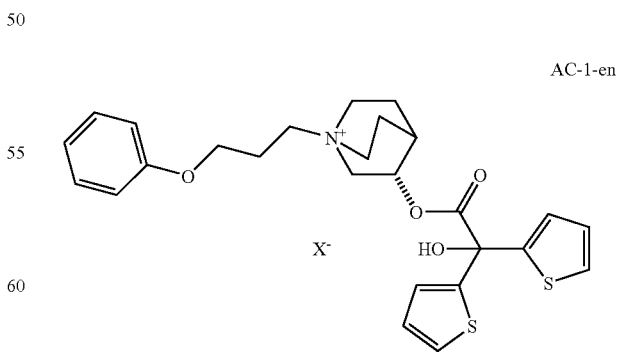

AC-1-en wherein $X^-$ may have the above-mentioned meanings. Other preferred anticholinergics are selected from the salts of formula AC-2

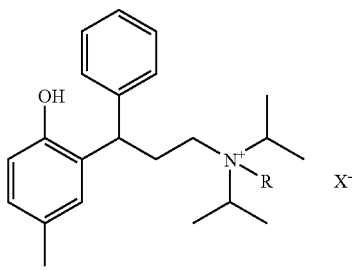

AC-2 wherein R denotes either methyl or ethyl and wherein X⁻ may have the above-mentioned meanings. In an alternative embodiment the compound of formula AC-2 may also be present in the form of the free base AC-2-base.

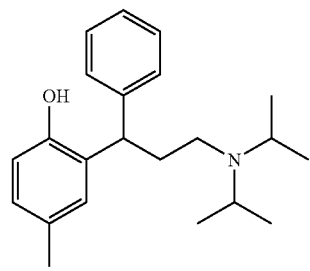

AC-2-base

Other specified compounds are:
tropenol 2,2-diphenylpropionate methobromide,
scopine 2,2-diphenylpropionate methobromide,
scopine 2-fluoro-2,2-diphenylacetate methobromide,
tropenol 2-fluoro-2,2-diphenylacetate methobromide;
tropenol 3,3',4,4'-tetrafluorobenzilate methobromide,
scopine 3,3',4,4'-tetrafluorobenzilate methobromide,
tropenol 4,4'-difluorobenzilate methobromide,
scopine 4,4'-difluorobenzilate methobromide,
tropenol 3,3'-difluorobenzilate methobromide,
scopine 3,3'-difluorobenzilate methobromide;
tropenol 9-hydroxy-fluorene-9-carboxylate methobromide;
tropenol 9-fluoro-fluorene-9-carboxylate methobromide;
scopine 9-hydroxy-fluorene-9-carboxylate methobromide;
scopine 9-fluoro-fluorene-9-carboxylate methobromide;
tropenol 9-methyl-fluorene-9-carboxylate methobromide;
scopine 9-methyl-fluorene-9-carboxylate methobromide;
cyclopropyltropine benzilate methobromide;
cyclopropyltropine 2,2-diphenylpropionate methobromide;
cyclopropyltropine 9-hydroxy-xanthene-9-carboxylate methobromide;
cyclopropyltropine 9-methyl-fluorene-9-carboxylate methobromide;
cyclopropyltropine 9-methyl-xanthene-9-carboxylate methobromide;
cyclopropyltropine 9-hydroxy-fluorene-9-carboxylate methobromide;
cyclopropyltropine methyl 4,4'-difluorobenzilate methobromide.
tropenol 9-hydroxy-xanthene-9-carboxylate methobromide;
scopine 9-hydroxy-xanthene-9-carboxylate methobromide;
tropenol 9-methyl-xanthene-9-carboxylate-methobromide;
scopine 9-methyl-xanthene-9-carboxylate-methobromide;
tropenol 9-ethyl-xanthene-9-carboxylate methobromide;
tropenol 9-difluoromethyl-xanthene-9-carboxylate methobromide;
scopine 9-hydroxymethyl-xanthene-9-carboxylate methobromide, The above-mentioned compounds may also be used as salts within the scope of the present invention, wherein instead of the methobromide the salts metho-X are used, wherein X may have the meanings given hereinbefore for X⁻.

As corticosteroids it is preferable to use compounds selected from among beclomethasone, betamethasone, budesonide, butixocort, ciclesonide, deflazacort, dexamethasone, etiprednol, flunisolide, fluticasone, loteprednol, mometasone, prednisolone, prednisone, rofleponide, triamcinolone, RPR-106541, NS-126, ST-26 and
(S)-fluoromethyl 6,9-difluoro-17-[(2-furanylcarbonyl)oxy]-11-hydroxy-16-methyl-3-oxo-androsta-1,4-diene-17-carbothionate
(S)-(2-oxo-tetrahydro-furan-3 S-yl)6,9-difluoro-11-hydroxy-16-methyl-3-oxo-17-propionyloxy-androsta-1,4-diene-17-carbothionate,
cyanomethyl 6α,9α-difluoro-11β-hydroxy-16α-methyl-3-oxo-17α-(2,2,3,3-tertamethylcyclopropylcarbonyl)oxy-androsta-1,4-diene-17β-carboxylate
optionally in the form of the racemates, enantiomers or diastereomers thereof and optionally in the form of the salts and derivatives thereof, the solvates and/or hydrates thereof. Any reference to steroids includes a reference to any salts or derivatives, hydrates or solvates thereof which may exist. Examples of possible salts and derivatives of the steroids may be: alkali metal salts, such as, for example, sodium or potassium salts, sulphobenzoates, phosphates, isonicotinates, acetates, dichloroacetates, propionates, dihydrogen phosphates, palmitates, pivalates or furoates.

PDE4-inhibitors which may be used are preferably compounds selected from among enprofyllin, theophyllin, roflumilast, ariflo (cilomilast), tofimilast, pumafentrin, lirimilast, arofyllin, atizoram, D-4418, Bay-198004, BY343, CP-325.366, D-4396 (Sch-351591), AWD-12-281 (GW-842470), NCS-613, CDP-840, D-4418, PD-168787, T-440, T-2585, V-11294A, C1-1018, CDC-801, CDC-3052, D-22888, YM-58997, Z-15370 and
N-(3,5-dichloro-1-oxo-pyridin-4-yl)-4-difluoromethoxy-3-cyclopropylmethoxybenzamide
(−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide
(R)-(+)-1-(4-bromobenzyl)-4-[(3-cyclopentyloxy)-4-methoxyphenyl]-2-pyrrolidone
3-(cyclopentyloxy-4-methoxyphenyl)-1-(4-N'-[N-2-cyano-5-methyl-isothioureido]benzyl)-2-pyrrolidone
cis[4-cyano-4-(3-cyclopentyloxy-4-methoxyphenyl)cyclohexane-1-carboxylic acid]
2-carbomethoxy-4-cyano-4-(3-cyclopropylmethoxy-4-difluoromethoxy-phenyl)cyclohexan-1-one
cis[4-cyano-4-(3-cyclopropylmethoxy-4-difluoromethoxyphenyl)cyclohexan-1-ol]
(R)-(+)-ethyl[4-(3-cyclopentyloxy-4-methoxyphenyl)pyrrolidin-2-ylidene]acetate
(S)-(−)-ethyl[4-(3-cyclopentyloxy-4-methoxyphenyl)pyrrolidin-2-ylidene]acetate
9-cyclopentyl-5,6-dihydro-7-ethyl-3-(2-thienyl)-9H-pyrazolo[3,4-c]-1,2,4-triazolo[4.3-a]pyridine
9-cyclopentyl-5,6-dihydro-7-ethyl-3-(tert-butyl)-9H-pyrazolo[3,4-c]-1,2,4-triazolo[4.3-a]pyridine
optionally in the form of the racemates, enantiomers or diastereomers thereof and optionally in the form of the pharmacologically acceptable acid addition salts thereof, the solvates and/or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The LTD4-antagonists used are preferably compounds selected from among montelukast, pranlukast, zafirlukast, MCC-847 (ZD-3523), MN-001, MEN-91507 (LM-1507), VUF-5078, VUF-K-8707, L-733321 and 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)methyl)cyclopropaneacetic acid

[2-[[2-(4-tert-butyl-2-thiazolyl)-5-benzofuranyl]oxymethyl] phenyl]acetic acid optionally in the form of the racemates, enantiomers or diastereomers thereof and optionally in the form of the pharmacologically acceptable acid addition salts, solvates and/or hydrates thereof. According to the invention the acid addition salts of the betamimetics are preferably selected from among the hydrochloride, hydrobromide, hydroiodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate. By salts or derivatives which the LTD4-antagonists may optionally be capable of forming are meant, for example: alkali metal salts, such as for example sodium or potassium salts, alkaline earth metal salts, sulphobenzoates, phosphates, isonicotinates, acetates, propionates, dihydrogen phosphates, palmitates, pivalates or furoates.

EGFR-inhibitors which may be used are preferably compounds selected from among cetuximab, trastuzumab, ABX-EGF, Mab ICR-62 and 4-[(3-chloro-4-fluorophenyl)amino]-6-{[4-(morpholin-4-yl)-1-oxo-2-buten-1-yl]amino}-7-cyclopropylmethoxy-quinazoline 4-[(3-chloro-4-fluorophenyl)amino]-6-{[4-(N,N-diethylamino)-1-oxo-2-buten-1-yl]-amino}-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopropylmethoxy-quinazoline 4-[(R)-(1-phenyl-ethyl)amino]-6-{[4-(morpholin-4-yl)-1-oxo-2-buten-1-yl]amino}-7-cyclopentyloxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-cyclopropylmethoxy-quinazoline 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline 4-[(3-chloro-4-fluoro-phenyl)amino]-6-{[4-((R)-2-methoxymethyl-6-oxo-morpholin-4-yl)-1-oxo-2-buten-1-yl]amino}-7-cyclopropylmethoxy-quinazoline 4-[(3-chloro-4-fluoro-phenyl)amino]-6-[2-((S)-6-methyl-2-oxo-morpholin-4-yl)-ethoxy]-7-methoxy-quinazoline 4-[(3-chloro-4-fluorophenyl)amino]-6-({4-[N-(2-methoxyethyl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-cyclopentyloxy-quinazoline 4-[(R)-(1-phenyl-ethyl)amino]-6-{[4-(N,N-to-(2-methoxyethyl)-amino]-1-oxo-2-buten-1-yl]amino}-7-cyclopropylmethoxy-quinazoline 4-[(R)-(1-phenyl-ethyl)amino]-6-({4-[N-(2-methoxyethyl)-N-ethyl-amino]-1-oxo-2-buten-1-yl}amino)-7-cyclopropylmethoxy-quinazoline 4-[(R)-(1-phenyl-ethyl)amino]-6-({4-[N-(2-methoxyethyl)-N-methyl-amino]-1-oxo-2-buten-1-yl}amino)-7-cyclopropylmethoxy-quinazoline 4-[(R)-(1-phenyl-ethyl)amino]-6-({4-[N-(tetrahydropyran-4-yl)-N-methyl-amino]-1-oxo-2-buten-1-yl}amino)-7-cyclopropylmethoxy-quinazoline 4-[(3-chloro-4-fluorophenyl)amino]-6-{[4-(N,N-dimethylamino)-1-oxo-2-buten-1-yl]amino}-7-((R)-tetrahydrofuran-3-yloxy)-quinazoline 4-[(3-chloro-4-fluorophenyl)amino]-6-{[4-(N,N-dimethylamino)-1-oxo-2-buten-1-yl]amino}-7-((S)-tetrahydrofuran-3-yloxy)-quinazoline 4-[(3-chloro-4-fluorophenyl)amino]-6-({4-[N-(2-methoxyethyl)-N-methyl-amino]-1-oxo-2-buten-1-yl}amino)-7-cyclopentyloxy-quinazoline 4-[(3-chloro-4-fluorophenyl)amino]-6-{[4-(N-cyclopropyl-N-methyl-amino)-1-oxo-2-buten-1-yl]amino}-7-cyclopentyloxy-quinazoline 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline 4-[(3-chloro-4-fluorophenyl)amino]-6-{[4-(N,N-dimethylamino)-1-oxo-2-buten-1-yl]amino}-7-[(S)-(tetrahydrofuran-2-yl)methoxy]-quinazoline 4-[(3-ethynyl-phenyl)amino]-6.7-to-(2-methoxy-ethoxy)-quinazoline 4-[(3-chloro-4-fluorophenyl)amino]-7-[3-(morpholin-4-yl)-propyloxy]-6-[(vinyl-carbonyl)amino]-quinazoline 4-[(R)-(1-phenyl-ethyl)amino]-6-(4-hydroxy-phenyl)-7H-pyrrolo[2,3-d]pyrimidine 3-cyano-4-[(3-chloro-4-fluorophenyl)amino]-6-{[4-(N,N-dimethylamino)-1-oxo-2-buten-1-yl]amino}-7-ethoxy-quinoline 4-{[3-chloro-4-(3-fluoro-benzyloxy)-phenyl]amino}-6-(5-{[(2-methanesulphonyl-ethyl)amino]methyl}-furan-2-yl) quinazoline 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline 4-[(3-chloro-4-fluorophenyl)amino]-6-({4-[N,N-to-(2-methoxy-ethyl)-amino]-1-oxo-2-buten-1-yl}amino)-7-[(tetrahydrofuran-2-yl)methoxy]-quinazoline 4-[(3-ethynyl-phenyl)amino]-6-{[4-(5.5-dimethyl-2-oxo-morpholin-4-yl)-1-oxo-2-buten-1-yl]amino}-quinazoline 4-[(3-chloro-4-fluoro-phenyl)amino]-6-[2-(2,2-dimethyl-6-oxo-morpholin-4-yl)-ethoxy]-7-methoxy-quinazoline 4-[(3-chloro-4-fluoro-phenyl)amino]-6-[2-(2,2-dimethyl-6-oxo-morpholin-4-yl)-ethoxy]-7-[(R)-(tetrahydrofuran-2-yl)methoxy]-quinazoline 4-[(3-chloro-4-fluoro-phenyl)amino]-7-[2-(2,2-dimethyl-6-oxo-morpholin-4-yl)-ethoxy]-6-[(S)-(tetrahydrofuran-2-yl)methoxy]-quinazoline 4-[(3-chloro-4-fluoro-phenyl)amino]-6-{2-[4-(2-oxo-morpholin-4-yl)-piperidin-1-yl]-ethoxy}-7-methoxy-quinazoline 4-[(3-chloro-4-fluoro-phenyl)amino]-6-[1-(tert.-butyloxycarbonyl)-piperidin-4-yloxy]-7-methoxy-quinazoline 4-[(3-chloro-4-fluoro-phenyl)amino]-6-(trans-4-amino-cyclohexan-1-yloxy)-7-methoxy-quinazoline
4-[(3-chloro-4-fluoro-phenyl)amino]-6-(trans-4-methanesulphonylamino-cyclohexan-1-yloxy)-7-methoxy-quinazoline
4-[(3-chloro-4-fluoro-phenyl)amino]-6-(tetrahydropyran-3-yloxy)-7-methoxy-quinazoline
4-[(3-chloro-4-fluoro-phenyl)amino]-6-(1-methyl-piperidin-4-yloxy)-7-methoxy-quinazoline
4-[(3-chloro-4-fluoro-phenyl)amino]-6-{1-[(morpholin-4-yl)carbonyl]-piperidin-4-yl-oxy}-7-methoxy-quinazoline
4-[(3-chloro-4-fluoro-phenyl)amino]-6-{1-[(methoxymethyl)carbonyl]-piperidin-4-yl-oxy}-7-methoxy-quinazoline
4-[(3-chloro-4-fluoro-phenyl)amino]-6-(piperidin-3-yloxy)-7-methoxy-quinazoline
4-[(3-chloro-4-fluoro-phenyl)amino]-6-[1-(2-acetylamino-ethyl)-piperidin-4-yloxy]-7-methoxy-quinazoline
4-[(3-chloro-4-fluoro-phenyl)amino]-6-(tetrahydropyran-4-yloxy)-7-ethoxy-quinazoline
4-[(3-chloro-4-fluoro-phenyl)amino]-6-((S)-tetrahydrofuran-3-yloxy)-7-hydroxy-quinazoline
4-[(3-chloro-4-fluoro-phenyl)amino]-6-(tetrahydropyran-4-yloxy)-7-(2-methoxy-ethoxy)-quinazoline
4-[(3-chloro-4-fluoro-phenyl)amino]-6-{trans-4-[(dimethylamino)sulphonylamino]-cyclohexan-1-yloxy}-7-methoxy-quinazoline
4-[(3-chloro-4-fluoro-phenyl)amino]-6-{trans-4-[(morpholin-4-yl)carbonylamino]-cyclohexan-1-yloxy}-7-methoxy-quinazoline
4-[(3-chloro-4-fluoro-phenyl)amino]-6-{trans-4-[(morpholin-4-yl)sulphonylamino]-cyclohexan-1-yloxy}-7-methoxy-quinazoline
4-[(3-chloro-4-fluoro-phenyl)amino]-6-(tetrahydropyran-4-yloxy)-7-(2-acetylamino-ethoxy)-quinazoline
4-[(3-chloro-4-fluoro-phenyl)amino]-6-(tetrahydropyran-4-yloxy)-7-(2-methanesulphonylamino-ethoxy)-quinazoline
4-[(3-chloro-4-fluoro-phenyl)amino]-6-{1-[(piperidin-1-yl)carbonyl]-piperidin-4-yloxy}-7-methoxy-quinazoline
4-[(3-chloro-4-fluoro-phenyl)amino]-6-(1-aminocarbonylmethyl-piperidin-4-yloxy)-7-methoxy-quinazoline
4-[(3-chloro-4-fluoro-phenyl)amino]-6-(cis-4-{N-[(tetrahydropyran-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline
4-[(3-chloro-4-fluoro-phenyl)amino]-6-(cis-4-{N-[(morpholin-4-yl)sulphonyl]-N-methyl-amino}-cyclohexan-1-yloxy)-7-methoxy-quinazoline
4-[(3-chloro-4-fluoro-phenyl)amino]-6-(trans-4-ethanesulphonylamino-cyclohexan-1-yloxy)-7-methoxy-quinazoline
4-[(3-chloro-4-fluoro-phenyl)amino]-6-(1-methanesulphonyl-piperidin-4-yloxy)-7-ethoxy-quinazoline
4-[(3-chloro-4-fluoro-phenyl)amino]-6-(1-methanesulphonyl-piperidin-4-yloxy)-7-(2-methoxy-ethoxy)-quinazoline
4-[(3-chloro-4-fluoro-phenyl)amino]-6-[1-(2-methoxy-acetyl)-piperidin-4-yloxy]-7-(2-methoxy-ethoxy)-quinazoline
4-[(3-chloro-4-fluoro-phenyl)amino]-6-(cis-4-acetylamino-cyclohexan-1-yloxy)-7-methoxy-quinazoline
4-[(3-ethynyl-phenyl)amino]-6-[1-(tert.-butyloxycarbonyl)-piperidin-4-yloxy]-7-methoxy-quinazoline
4-[(3-ethynyl-phenyl)amino]-6-(tetrahydropyran-4-yloxy)-7-methoxy-quinazoline
4-[(3-chloro-4-fluoro-phenyl)amino]-6-(cis-4-{N-[(piperidin-1-yl)carbonyl]-N-methyl-amino}-cyclohexan-1-yloxy)-7-methoxy-quinazoline
4-[(3-chloro-4-fluoro-phenyl)amino]-6-(cis-4-{N-[(4-methyl-piperazin-1-yl)carbonyl]-N-methyl-amino}-cyclohexan-1-yloxy)-7-methoxy-quinazoline
4-[(3-chloro-4-fluoro-phenyl)amino]-6-{cis-4-[(morpholin-4-yl)carbonylamino]-cyclohexan-1-yloxy}-7-methoxy-quinazoline
4-[(3-chloro-4-fluoro-phenyl)amino]-6-{1-[2-(2-oxopyrrolidin-1-yl)ethyl]-piperidin-4-yloxy}-7-methoxy-quinazoline
4-[(3-chloro-4-fluoro-phenyl)amino]-6-{1-[(morpholin-4-yl)carbonyl]-piperidin-4-yloxy}-7-(2-methoxy-ethoxy)-quinazoline
4-[(3-ethynyl-phenyl)amino]-6-(1-acetyl-piperidin-4-yloxy)-7-methoxy-quinazoline
4-[(3-ethynyl-phenyl)amino]-6-(1-methyl-piperidin-4-yloxy)-7-methoxy-quinazoline
4-[(3-ethynyl-phenyl)amino]-6-(1-methanesulphonyl-piperidin-4-yloxy)-7-methoxy-quinazoline
4-[(3-chloro-4-fluoro-phenyl)amino]-6-(1-methyl-piperidin-4-yloxy)-7-(2-methoxy-ethoxy)-quinazoline
4-[(3-chloro-4-fluoro-phenyl)amino]-6-(1-isopropyloxycarbonyl-piperidin-4-yloxy)-7-methoxy-quinazoline
4-[(3-chloro-4-fluoro-phenyl)amino]-6-(cis-4-methylamino-cyclohexan-1-yloxy)-7-methoxy-quinazoline
4-[(3-chloro-4-fluoro-phenyl)amino]-6-{cis-4-[N-(2-methoxy-acetyl)-N-methyl-amino]-cyclohexan-1-yloxy}-7-methoxy-quinazoline
4-[(3-ethynyl-phenyl)amino]-6-(piperidin-4-yloxy)-7-methoxy-quinazoline
4-[(3-ethynyl-phenyl)amino]-6-[1-(2-methoxy-acetyl)-piperidin-4-yloxy]-7-methoxy-quinazoline
4-[(3-ethynyl-phenyl)amino]-6-{1-[(morpholin-4-yl)carbonyl]-piperidin-4-yloxy}-7-methoxy-quinazoline
4-[(3-chloro-4-fluoro-phenyl)amino]-6-{1-[(cis-2,6-dimethyl-morpholin-4-yl)carbonyl]-piperidin-4-yloxy}-7-methoxy-quinazoline
4-[(3-chloro-4-fluoro-phenyl)amino]-6-{1-[(2-methyl-morpholin-4-yl)carbonyl]-piperidin-4-yloxy}-7-methoxy-quinazoline
4-[(3-chloro-4-fluoro-phenyl)amino]-6-{1-[(S,S)-(2-oxa-5-aza-bicyclo[2,2,1]hept-5-yl)carbonyl]-piperidin-4-yloxy}-7-methoxy-quinazoline
4-[(3-chloro-4-fluoro-phenyl)amino]-6-{1-[(N-methyl-N-2-methoxyethyl-amino)carbonyl]-piperidin-4-yloxy-}-7-methoxy-quinazoline
4-[(3-chloro-4-fluoro-phenyl)amino]-6-(1-ethyl-piperidin-4-yloxy)-7-methoxy-quinazoline
4-[(3-chloro-4-fluoro-phenyl)amino]-6-{1-[(2-methoxyethyl)carbonyl]-piperidin-4-yloxy}-7-methoxy-quinazoline
4-[(3-chloro-4-fluoro-phenyl)amino]-6-{1-[(3-methoxypropyl-amino)-carbonyl]-piperidin-4-yloxy}-7-methoxy-quinazoline
4-[(3-chloro-4-fluoro-phenyl)amino]-6-[cis-4-(N-methanesulphonyl-N-methyl-amino)-cyclohexan-1-yloxy]-7-methoxy-quinazoline
4-[(3-chloro-4-fluoro-phenyl)amino]-6-[cis-4-(N-acetyl-N-methyl-amino)-cyclohexan-1-yloxy]-7-methoxy-quinazoline
4-[(3-chloro-4-fluoro-phenyl)amino]-6-(trans-4-methylamino-cyclohexan-1-yloxy)-7-methoxy-quinazoline 4-[(3-chloro-4-fluoro-phenyl)amino]-6-[trans-4-(N-methanesulphonyl-N-methyl-amino)-cyclohexan-1-yloxy]-7-methoxy-quinazoline 4-[(3-chloro-4-fluoro-phenyl)amino]-6-(trans-4-dimethylamino-cyclohexan-1-yloxy)-7-methoxy-quinazoline 4-[(3-chloro-4-fluoro-phenyl)amino]-6-(trans-4-{N-[(morpholin-4-yl)carbonyl]-N-methyl-amino}-cyclohexan-1-yloxy)-7-methoxy-quinazoline 4-[(3-chloro-4-fluoro-phenyl)amino]-6-[2-(2,2-dimethyl-6-oxo-morpholin-4-yl)-ethoxy]

7-[(S)-(tetrahydrofuran-2-yl)methoxy]-quinazoline

4-[(3-chloro-4-fluoro-phenyl)amino]-6-(1-methanesulphonyl-piperidin-4-yloxy)-7-methoxy-quinazoline 4-[(3-chloro-4-fluoro-phenyl)amino]-6-(1-cyano-piperidin-4-yloxy)-7-methoxy-quinazoline optionally in the form of the racemates, enantiomers, diastereomers thereof and optionally in the form of the pharmacologically acceptable acid addition salts, solvates or hydrates thereof. According to the invention, the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

The dopamine agonists used are preferably compounds selected from among bromocriptin, cabergoline, alpha-dihydroergocryptine, lisuride, pergolide, pramipexol, roxindol, ropinirol, talipexol, tergurid and viozan, optionally in the form of the racemates, enantiomers, diastereomers thereof, and optionally, in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydrooxalate, hydrosuccinate, hydrobenzoate and hydro-p-toluenesulphonate.

H1-Antihistamines which may be used are preferably compounds selected from among epinastine, cetirizine, azelastine, fexofenadine, levocabastine, loratadine, mizolastine, ketotifen, emedastine, dimetindene, clemastine, bamipine, cexchlorpheniramine, pheniramine, doxylamine, chlorphenoxamine, dimenhydrinate, diphenhydramine, promethazine, ebastine, desloratidine and meclozine, optionally in the form of the racemates, enantiomers, diastereomers thereof, and optionally, in the form of the pharmacologically acceptable acid addition salts, solvates or hydrates thereof. According to the invention the acid addition salts of the betamimetics are preferably selected from among the hydrochloride, hydrobromide, hydriodide, hydrosulphate, hydrophosphate, hydromethanesulphonate, hydronitrate, hydromaleate, hydroacetate, hydrocitrate, hydrofumarate, hydrotartrate, hydroxalate, hydrosuccinate, hydrobenzoate and hydro-p-toluenesulphonate.

It is also possible to use inhalable macromolecules, as disclosed in European Patent Application EP 1 003 478 A1 or Canadian Patent Application CA 2297174 A1.

In addition, the compounds may come from the groups of ergot alkaloid derivatives, the triptans, the CGRP-inhibitors, the phosphodiesterase-V inhibitors, optionally in the form of the racemates, enantiomers or diastereomers thereof, optionally in the form of the pharmacologically acceptable acid addition salts, the solvates and/or hydrates thereof.

Examples of ergot alkaloid derivatives are dihydroergotamine and ergotamine.

The invention claimed is:

1. Dispensing device for dispensing a formulation as a spray, comprising:
    a storage device with multiple separate and pre-metered doses of the formulation in annularly arranged receptacles,
    a transport mechanism for indexing the storage device provided with the receptacles,
    a release button for triggering the dispensing device, and
    at least one lifespan blocking means for preventing operating of the dispensing device after a predetermined number of uses corresponding to the number of receptacles,
    wherein the storage device comprises a snap portion forming one of the at least one lifespan blocking means which locks the release button in an actuated state when the storage device is in a position for dispensing the formulation from a last of the receptacles.

2. Dispensing device for dispensing a formulation as a spray, according to claim 1, wherein said at least one lifespan blocking means comprises three lifespan blocking means.

3. Dispensing device according to claim 1, wherein the storage device comprises an abutment forming a second lifespan blocking means of the at least one lifespan blocking means and stopping any further movement or indexing of the storage device by abutment to a stationary counterstop when the storage device has reached a position for dispensing the formulation from the last receptacle.

4. Dispensing device according to claim 1, further comprising a means for pressurizing gas for dispensing the formulation.

5. Dispensing device according to claim 4, wherein the means for pressurizing gas comprises a manually operated air pump.

6. Dispensing device according to claim 4, wherein the means for pressurizing gas comprises a spring store for compressing the gas.

7. Dispensing device according to claim 4, wherein the means for pressurizing gas is actuatable, for producing a gas stream for dispensing of a dose, by the release button.

8. Dispensing device according to claim 4, further comprising a manually operated actuator for actuating at least one of the transport mechanism and the means for pressurizing gas.

9. Dispensing device according to claim 1, further comprising a connecting element that is moveable relative to the receptacles for individually connecting to each of the receptacles for supplying the pressurized gas to the respective receptacle to dispense the respective dose of formulation.

10. Dispensing device according to claim 9, wherein the connecting element is a piercing element for piercing the respective receptacle.

11. Dispensing device according to claim 1, wherein each receptacle comprises a moveable insert which contains a respective dose of formulation.

12. Dispensing device according to claim 11, further comprising a connecting element that is moveable relative to the receptacles for individually connecting to the insert of each of the receptacles for supplying the pressurized gas to the respective insert to dispense the respective dose of formulation.

13. Dispensing device according to claim 12, wherein the connecting element is a piercing element for piercing the respective insert.

14. Dispensing device according to claim 11, wherein each insert comprises at least one channel or nozzle arrangement, wherein the channel or nozzle arrangement directly forms the spray during use.

15. Dispensing device according to claim 1, wherein the dispensing device is a dry powder inhaler.

16. Dispensing device for dispensing a formulation as a spray, comprising:
- a storage device with multiple separate and pre-metered doses of the formulation in annularly arranged receptacles,
- a transport mechanism for indexing the storage device provided with the receptacles,
- a means for pressurizing gas for dispensing the formulation,
- a manually operated actuator for actuating at least one of the transport mechanism and the means for pressurizing gas, and
- at least one lifespan blocking means for preventing operating of the dispensing device after a predetermined number of uses corresponding to the number of receptacles,
- wherein the storage device comprises a snap hook forming one of the at least one lifespan blocking means, the snap hook being adapted for locking the actuator in a pushed-in or depressed state when the storage device has reached a position for dispensing the formulation from a last of the receptacles.

17. Dispensing device for dispensing a formulation as a spray, according to claim 16, wherein said at least one lifespan blocking means comprises three lifespan blocking means.

18. Dispensing device according to claim 16, wherein the storage device comprises an abutment forming a second lifespan blocking means of the at least one lifespan blocking means and stopping any further movement or indexing of the storage device by abutment to a stationary counterstop when the storage device has reached a position for dispensing the formulation from the last receptacle.

19. Dispensing device according to claim 16, wherein the means for pressurizing gas comprises a manually operated air pump.

20. Dispensing device according to claim 16, wherein the means for pressurizing gas is actuatable, for producing a gas stream for dispensing of a dose, by a release button.

21. Dispensing device according to claim 16, further comprising a connecting element that is moveable relative to the receptacles for individually connecting to each of the receptacles for supplying the pressurized gas to the respective receptacle to dispense the respective dose of formulation.

22. Dispensing device according to claim 21, wherein the connecting element is a piercing element for piercing the respective receptacle.

23. Dispensing device according to claim 16, wherein each receptacle comprises a moveable insert which contains a respective dose of formulation.

24. Dispensing device according to claim 23, further comprising a connecting element that is moveable relative to the receptacles for individually connecting to the insert of each of the receptacles for supplying the pressurized gas to the respective insert to dispense the respective dose of formulation.

25. Dispensing device according to claim 24, wherein the connecting element is a piercing element for piercing the respective insert.

26. Dispensing device according to claim 23, wherein each insert comprises at least one channel or nozzle arrangement, wherein the channel or nozzle arrangement directly forms the spray during use.

27. Dispensing device according to claim 16, wherein the dispensing device is a dry powder inhaler.

28. Dispensing device for dispensing a formulation as a spray, comprising:
- a storage device with multiple separate and pre-metered doses of the formulation in annularly arranged receptacles,
- a transport mechanism for indexing the storage device provided with the receptacles,
- a means for pressurizing gas for dispensing the formulation,
- a manually operated actuator for actuating at least one of the transport mechanism and the means for pressurizing gas,
- a release button for triggering the dispensing device, and
- at least two lifespan blocking means for preventing operating of the dispensing device after a predetermined number of uses corresponding to the number of receptacles, wherein one of the at least two lifespan blocking means is a button locking means that is adapted to lock the release button, and a second of the at least two lifespan blocking means is a further locking means that is adapted to lock indexing of the storage device or lock the actuator.

29. Dispensing device according to claim 28, wherein the means for pressurizing gas comprises a manually operated air pump.

30. Dispensing device according to claim 28, wherein the means for pressurizing gas comprises a spring store for compressing the gas.

31. Dispensing device according to claim 29, wherein the means for pressurizing gas is actuable, for producing a gas stream for dispensing of a dose, by the release bottom.

32. Dispensing device according to claim 28, wherein the button locking means comprises a snap portion at the storage device for locking the release button in an actuated state when the storage device is in a position for dispensing the formulation from a last one of the receptacles.

33. Dispensing device according to claim 28, wherein the further locking means is a storage locking means, the storage locking means being adapted to lock indexing of the storage device.

34. Dispensing device according to claim 33, wherein the further locking means comprises an abutment at the storage device for stopping any further indexing of the storage device by abutment to a stationary counterstop when the storage device has reached a position for dispensing the formulation from a the last one of the receptacles.

35. Dispensing device according to claim 28, wherein the further locking means is an actuator lock that is adapted to lock the actuator.

36. Dispensing device according to claim 35, wherein the actuator lock comprises a snap hook at the storage device that is adapted for locking the actuator in a pushed-in or depressed state when the storage device has reached a position for dispensing the formulation from a last one of the receptacles.

37. Dispensing device for dispensing a formulation as a spray, according to claim 28, further comprising a third lifespan blocking means.

38. Dispensing device for dispensing a formulation as a spray, according to claim 28, further comprising a connecting element that is moveable relative to the receptacles for individually connecting to each of the receptacles for supplying the pressurized gas to the respective receptacle to dispense the respective dose of formulation.

39. Dispensing device according to claim 38, wherein the connecting element is a piercing element for piercing the respective receptacle.

40. Dispensing device according to claim 28, wherein each receptacle comprises a moveable insert which contains a respective dose of formulation.

41. Dispensing device according to claim 40, further comprising a connecting element that is moveable relative to the receptacles for individually connecting to the insert of each of the receptacles for supplying the pressurized gas to the respective insert to dispense the respective dose of formulation.

42. Dispensing device according to claim 41, wherein the connecting element is a piercing element for piercing the respective insert.

43. Dispensing device according to claim 40, wherein each insert comprises at least one channel or nozzle arrangement, and wherein the channel or nozzle arrangement directly forms the spray during use.

44. Dispensing device according to claim 28, wherein the dispensing device is a dry powder inhaler.

45. Dispensing device according to claim 28, wherein the further locking means comprises an abutment, the abutment being positioned for stopping any further movement of the storage device by engaging a stationary counterstop when the storage device has reached a position for dispensing the formulation from a last of the receptacles.

* * * * *